(12) United States Patent
Rohrer et al.

(10) Patent No.: US 9,693,539 B2
(45) Date of Patent: Jul. 4, 2017

(54) HCO32 AND HCO27 AND RELATED EXAMPLES

(75) Inventors: Daniel K. Rohrer, Los Gatos, CA (US); Nancy Amelia Black, Los Gatos, CA (US); Nils Lonberg, Woodside, CA (US)

(73) Assignee: E. R. SQUIBB & SONS, L.L.C., Princeton, NJ (US)

( * ) Notice: Subject to any disclaimer, the term of this patent is extended or adjusted under 35 U.S.C. 154(b) by 1685 days.

(21) Appl. No.: 12/672,883

(22) PCT Filed: Aug. 8, 2008

(86) PCT No.: PCT/US2008/072640
§ 371 (c)(1),
(2), (4) Date: Nov. 2, 2011

(87) PCT Pub. No.: WO2009/097006
PCT Pub. Date: Aug. 6, 2009

(65) Prior Publication Data
US 2012/0047585 A1    Feb. 23, 2012

Related U.S. Application Data

(60) Provisional application No. 60/955,194, filed on Aug. 10, 2007.

(51) Int. Cl.
| C12N 15/13 | (2006.01) |
| C12N 15/79 | (2006.01) |
| C12P 21/08 | (2006.01) |
| A01K 67/027 | (2006.01) |
| C07K 16/00 | (2006.01) |
| C12N 15/85 | (2006.01) |

(52) U.S. Cl.
CPC .......... *A01K 67/0275* (2013.01); *C07K 16/00* (2013.01); *C12N 15/8509* (2013.01); *A01K 2217/052* (2013.01); *A01K 2227/105* (2013.01); *A01K 2267/01* (2013.01); *C07K 2317/21* (2013.01); *C12N 2800/204* (2013.01)

(58) Field of Classification Search
CPC .......... C12N 15/8509; C12N 2800/204; A01K 67/0278; A01K 2227/105; A01K 2267/01
USPC .................... 435/320.1; 800/13, 18, 8, 6
See application file for complete search history.

(56) References Cited

U.S. PATENT DOCUMENTS

| 6,030,830 A | 2/2000 | Saxon et al. |
| 2003/0219439 A1 | 11/2003 | Reed et al. |
| 2004/0175721 A1 | 9/2004 | Doxsey et al. |
| 2005/0042664 A1 | 2/2005 | Wu et al. |
| 2005/0191293 A1 | 9/2005 | Deshpande et al. |
| 2006/0015957 A1 | 1/2006 | Lonberg et al. |
| 2006/0117398 A1 | 6/2006 | Buelow et al. |
| 2006/0156419 A1 | 7/2006 | Caton |
| 2007/0041976 A1 | 2/2007 | Pluenneke |

FOREIGN PATENT DOCUMENTS

| WO | WO94/25585 | 11/1994 |
| WO | WO2006122442 | 11/2006 |
| WO | WO 2007/117410 | 10/2007 |

OTHER PUBLICATIONS

Lonberg et al. (2005) Nat. Biotech., vol. 23(9),1117-1125.*
Harper (2004) Sci. Aging Knowl. Environ., vol. 5, as2.*
Bender et al., "Position independent and copy-number-related expression of the bovine neonatal Fc receptor α-chain in transgenic mice carrying a 102 kb BAC genomic fragment", *Transgenic Research*, 16(5):613-627, 2007.
Giraldo et al., "Size matters: use of YACs, BACs and PACs in transgenic animals", *Transgenic Research*, 10(2):83-103, 2001.
Jakobovits et al., "From XenoMouse technology to panitumumab, the first fully human antibody product from transgenic mice", *Nature Biotechnology*, 25(10):1134-1143, 2007.
Lonberg, "Fully human antibodies from transgenic mouse and phage display platforms", *Current Opinion in Immunology, Elsevier*, 20(4):450-459, 2008.
Lonberg, "Human antibodies from transgenic animals", *Nature Biotechnology*, 23(9):1117-1125, 2005.
Luby et al., "Sequences associated with the mouse Sμ switch region are important for immunoglobulin heavy chain transgene expression in B cell development", *European Journal of Immunology*, 31(10):2866-2875, 2001.
Sigurdardottir et al., "Regulatory regions 3' of the immunoglobulin heavy chain intronic enhancer differentially affect expression of a heavy chain transgene in resting and activated B cells", *The Journal of Immunology*, 154(5):2217-2225, 1995.
Supplementary European Search Report for EP Application No. EP 08 87 1709, dated Mar. 27, 2012 (corresponds to U.S. Appl. No. 12/672,883).
Alignment for AB01439.1 and AB019438.1, BAC end clone CIT-3054M17. NCBI (online) 1998 [retrieved on Jul. 24, 2009] retrieved from internet URL: http://www.ncbi.nlm.nih.gov/projects/genome/assembly/overlap/overlapview.cgi?acc1=AB019439.1 &acc2=AB019438.1, p. 3 of 6.

(Continued)

*Primary Examiner* — Anne Marie S Wehbe
(74) *Attorney, Agent, or Firm* — Baker Botts L.L.P.

(57) ABSTRACT

The instant invention relates to transgenic non-human animals capable of producing heterologous antibodies, transgenes used to produce such transgenic animals, transgenes capable of functionally rearranging a heterologous D gene in V-D-J recombination, immortalized B-cells capable of producing heterologous antibodies, methods and transgenes for producing heterologous antibodies of multiple isotypes, methods and transgenes for producing heterologous antibodies wherein a variable region sequence comprises somatic mutation as compared to germline rearranged variable region sequences, transgenic nonhuman animals which produce antibodies having a human primary sequence and which bind to human antigens, hybridomas made from B cells of such transgenic animals, and monoclonal antibodies expressed by such hybridomas.

7 Claims, 5 Drawing Sheets

(56) References Cited

OTHER PUBLICATIONS

Human chromosome 16-parm BAC clones from library D. Caltech [online] Jun. 8, 1998 [retrieved on Jul. 24, 2009] Retrieved from the internet URL: http://web.archive.org/web/2001082516348/www.tree.caltech.edu/cgi-bin/LIB.txtab?LIB_D_16q.txt. see clone 2194O15 p. 16.
AQ426717.1 CITBI-E1-2572O2.TR CITBI-E1 *Homo sapiens* genomic clone 2572O2, DNA sequence. GenBank (online) Created Mar. 23, 1999 [retrieved on Jul. 24, 2009] Retrieved from the internet URL: http://ncbi.nlm.nih.gov/nucgss/4499397?ordinalpos=1&itool=EntrezSystem2.PEntrez.Sequence.Sequence_ResultsPanel.Sequence_RVDocSum. See clone ID.
AQ019680.1. CIT-HSP-2304I22.TF CIT-HSP *Homo sapiens* genomic clone 2304I22, DNA Sequence. GenBank (online) Created Jun. 8, 1998 [retrieved on Jul. 24, 2009] Retrieved from the internet URL: http://www.nchi.nlm.nih.gov/nucgss/3198416?ordinalpos=1&itool=EntrezSystem2.PEntrez.Sequence.Sequence_ResultsPanel.Sequence_RVDocSum. See clone ID.
Sanchez-Iquierdo, D., et al., Detection of translocations affecting the BCL6 locus in B cell non-Hodgkin's lymphoma by interphase fluorescence in situ hybridization. Leukemia, 2001, vol. 15, pp. 1475-1484.

\* cited by examiner

Germline Transgenes: (YACs and BACs)

Hybrid Transgene: BAC VDJCE

Hybrid transgenes: BAC fusions

Hybrid Transgene: BAC V12DJCE

HCO32 AND HCO27 AND RELATED EXAMPLES

CROSS-REFERENCE TO RELATED APPLICATIONS

This application is a 35 U.S.C. 371 National Phase of International Application PCT/US08/072640, filed Aug. 8, 2008, which claims priority to U.S. Provisional Application Ser. No. 60/955,194, filed on Aug. 10, 2007, each of which are hereby incorporated by reference in their entirety herein.

SEQUENCE LISTING

The specification further incorporates by reference the Sequence Listing submitted herewith via EFS on Feb. 9, 2010. Pursuant to 37 C.F.R. §1.52(e)(5), the Sequence Listing text file, identified as 0773750876seqlist.txt, is 7,995 bytes and was created on Feb. 9, 2010. The Sequence Listing, electronically filed herewith, does not extend beyond the scope of the specification and thus does not contain new matter.

FIELD OF THE INVENTION

The invention relates to transgenic non-human animals capable of producing heterologous antibodies, transgenes used to produce such transgenic animals, transgenes capable of functionally rearranging a heterologous D gene in V-D-J recombination, immortalized B-cells capable of producing heterologous antibodies, methods and transgenes for producing heterologous antibodies of multiple isotypes, methods and transgenes for producing heterologous antibodies wherein a variable region sequence comprises somatic mutation as compared to germline rearranged variable region sequences, transgenic nonhuman animals which produce antibodies having a human primary sequence and which bind to human antigens, hybridomas made from B cells of such transgenic animals, and monoclonal antibodies expressed by such hybridomas.

BACKGROUND

One of the major impediments facing the development of in vivo therapeutic and diagnostic applications for monoclonal antibodies in humans is the intrinsic immunogenicity of non-human immunoglobulins. For example, when immunocompetent human patients are administered therapeutic doses of rodent monoclonal antibodies, the patients produce antibodies against the rodent immunoglobulin sequences; these human anti-mouse antibodies (HAMA) neutralize the therapeutic antibodies and can cause acute toxicity. Hence, it is desirable to produce human immunoglobulins that are reactive with specific human antigens that are promising therapeutic and/or diagnostic targets. However, producing human immunoglobulins that bind specifically with human antigens is problematic.

The construction of transgenic animals harboring a functional heterologous (e.g., human) immunoglobulin transgene is one method by which antibodies reactive with self antigens have been produced. However, in order to obtain expression of therapeutically useful antibodies, or hybridoma clones producing such antibodies, the transgenic animal must produce transgenic B cells that are capable of maturing through the B lymphocyte development pathway. While there are a number of examples of transgenic mice capable of maturing through that pathway and thereby undergoing functional V-D-J rearrangement to generate antibodies having both recombinational diversity and junctional diversity, such diversity is limited in comparison to the full genomic potential of any particular species.

In light of such limitations, a clear need exists for methods of efficiently producing heterologous antibodies having increased diversity, e.g. antibodies encoded by genetic sequences of a first species that are produced in a second species, which incorporate an increased fraction of the full genomic heavy and light chain variable region repertoires. There is also a need for a source of B cells which can be used to make hybridomas that produce monoclonal antibodies having such increased diversity for therapeutic or diagnostic use in the particular species for which they are designed.

SUMMARY OF THE INVENTION

In accordance with the foregoing objectives, transgenic nonhuman animals are provided which are capable of producing a heterologous antibody, such as a human antibody, which incorporate an increased fraction of the heavy and light chain variable region repertoires.

Further, it is an object to provide B-cells from such transgenic animals which are capable of expressing heterologous antibodies wherein such B-cells are immortalized to provide a source of a monoclonal antibody specific for a particular antigen.

In accordance with this foregoing object, it is a further object of the invention to provide hybridoma cells that are capable of producing such heterologous monoclonal antibodies.

Still further, it is an object herein to provide heterologous unrearranged immunoglobulin heavy and light chain transgenes useful for producing the aforementioned non-human transgenic animals.

Still further, it is an object herein to provide methods to disrupt endogenous immunoglobulin loci in the transgenic animals.

Still further, it is an object herein to provide methods to induce heterologous antibody production in the aforementioned transgenic non-human animal.

A further object of the invention is to provide methods to generate an immunoglobulin variable region gene segment repertoire that is used to construct one or more transgenes of the invention.

Human IgH BAC clones are shown below, in their relative positions and boundaries; these span the entire Vh region, D and J regions, up to and including the constant region Igα1.

FIG. 3. Schematic illustration of hybrid transgenes. FIG. 3A illustrates the BAC clones and Ig regions comprising BAC VDJCE. Constructed from BAC clones CTD-2590A7 and CTD-2194O15, with a tripartite enhancer from the downstream Ig enhancer LCR2, the construct contains all elements necessary for a functional minigene. FIG. 3B illustrates how the BAC clones covering the Vh region can be consolidated and modified to create a minimal set of BAC clones covering the entire Vh repertoire; addition of a 3' VHC homology cassette to each is meant to facilitate recombination between transgenes. FIG. 3C illustrates how BAC VDJCE was modified to incorporate the 12 Vh regions from plasmid pGP69-7 VHC, to create BAC V12DJCE. FIG. 3D illustrates how BAC VDJCE and YAC IgH10 can be recombined to form the transgene pIgYBAC; this is done in a modified shuttle vector that can be propogated in both yeast and bacteria.

Figure 4:
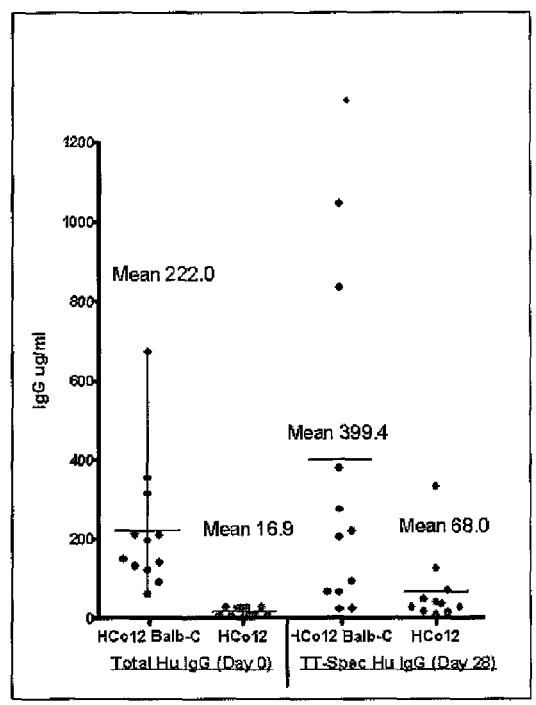

FIG. 4. Comparison of HCo12 and HCo12xBalb/c hybrid mice. HCo12 mice of the mixed strain background were compared to HCo12xBalb/c hybrid mice for baseline human immunoglobulin gamma (hu IgG) as well as tetanus-toxoid (TT) specific hu IgG. Cohorts (n=12 for each group) were bled at day 0, then immunized twice with TT and bled at day 28 post-immunization. Serum titers were determined for both mouse groups; HCo12 mice on the balb/c background showed significant elevations of both baseline total hu IgG and TT-specific hu IgG, compared to the parental HCo12 mixed background mice. Mean serum immunoglobulin levels (in µg/ml) are indicated for each group.

Figure 5:
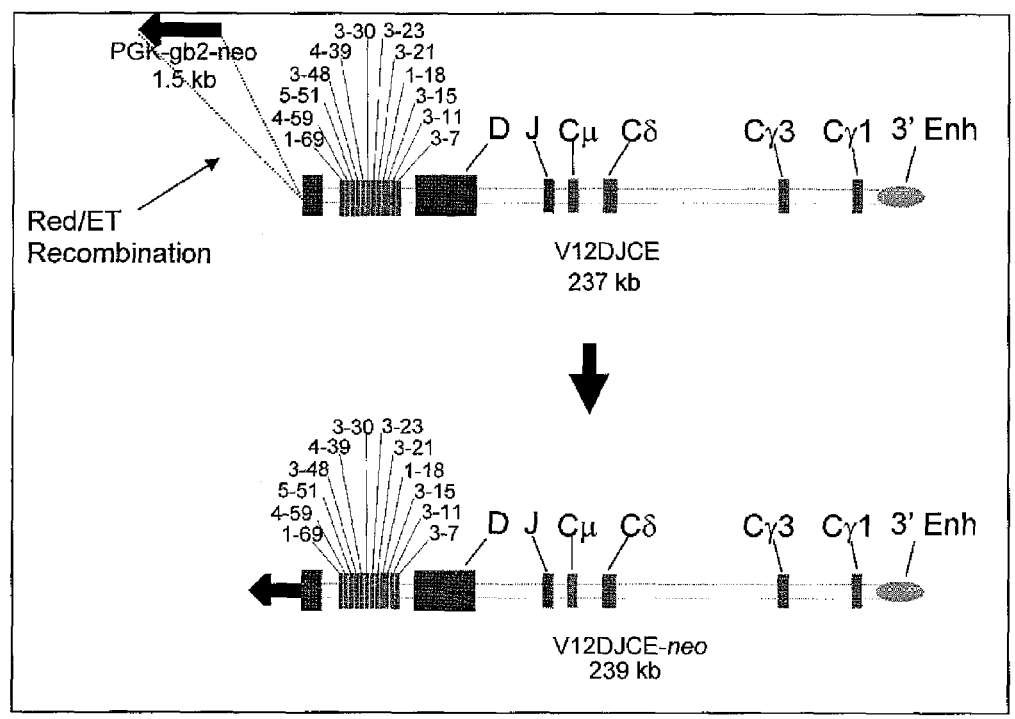

FIG. 5. Schematic illustration of Hybrid Transgene: BAC V12DJCE-neo. FIG. 5 illustrates the insertion of a selectable resistance marker from the neomycin resistance gene cassette (hereafter referred to as "neo"), operably linked to a dual prokaryotic and eukaryotic promoter/enhancer element, approximately 10 kb upstream of the 12 Vh variable-region gene segments present in BAC V12DJCE.

DETAILED DESCRIPTION

Definitions

As used herein, the term "antibody" refers to a glycoprotein comprising at least two light polypeptide chains and two heavy polypeptide chains. Each of the heavy and light polypeptide chains contains a variable region (generally the amino terminal portion of the polypeptide chain) which contains a binding domain which interacts with antigen. Each of the heavy and light polypeptide chains also comprises a constant region of the polypeptide chains (generally the carboxyl terminal portion) which may mediate the binding of the immunoglobulin to host tissues or factors including various cells of the immune system, some phagocytic cells and the first component (C1q) of the classical complement system.

As used herein, a "heterologous antibody" is defined in relation to the transgenic non-human organism producing such an antibody. It is defined as an antibody having an amino acid sequence or an encoding DNA sequence corresponding to that found in an organism not consisting of the transgenic non-human animal, and generally from a species other than that of the transgenic non-human animal.

As used herein, a "heterohybrid antibody" refers to an antibody having a light and heavy chains of different organismal origins. For example, an antibody having a human heavy chain associated with a murine light chain is a heterohybrid antibody.

As used herein, "isotype" refers to the antibody class (e.g., IgM or $IgG_1$) that is encoded by heavy chain constant region genes.

As used herein, "isotype switching" refers to the phenomenon by which the class, or isotype, of an antibody changes from one Ig class to one of the other Ig classes.

As used herein, "nonswitched isotype" refers to the isotypic class of heavy chain that is produced when no isotype switching has taken place; the $C_H$ gene encoding the nonswitched isotype is typically the first $C_H$ gene immediately downstream from the functionally rearranged VDJ gene.

As used herein, the term "switch sequence" refers to those DNA sequences responsible for switch recombination. A "switch donor" sequence, typically a µ switch region, will be 5' (i.e., upstream) of the construct region to be deleted during the switch recombination. The "switch acceptor" region will be between the construct region to be deleted and the replacement constant region (e.g., γ, ε, etc.). As there is no specific site where recombination always occurs, the final gene sequence will typically not be predictable from the construct.

As used herein, "glycosylation pattern" is defined as the pattern of carbohydrate units that are covalently attached to a protein, more specifically to an immunoglobulin protein. A glycosylation pattern of a heterologous antibody can be characterized as being substantially similar to glycosylation patterns which occur naturally on antibodies produced by the species of the nonhuman transgenic animal, when one of ordinary skill in the art would recognize the glycosylation pattern of the heterologous antibody as being more similar to said pattern of glycosylation in the species of the non-human transgenic animal than to the species from which the $C_H$ genes of the transgene were derived.

As used herein, "specific binding" refers to the property of the antibody: (1) to bind to a predetermined antigen with an affinity of at least $1 \times 10^7 M^{-1}$, and (2) to preferentially bind to the predetermined antigen with an affinity that is at least two-fold greater than its affinity for binding to a non-specific antigen (e.g., BSA, casein) other than the predetermined antigen or a closely-related antigen.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

The term "rearranged" as used herein refers to a configuration of a heavy chain or light chain immunoglobulin locus wherein a V segment is positioned immediately adjacent to a D-J or J segment in a conformation encoding essentially a complete $V_H$ or $V_L$ domain, respectively. A rearranged immunoglobulin gene locus can be identified by comparison to germline DNA; a rearranged locus will have at least one recombined heptamer/nonamer homology element.

The term "unrearranged" or "germline configuration" as used herein in reference to a V segment refers to the configuration wherein the V segment is not recombined so as to be immediately adjacent to a D or J segment.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98 to 99.5% of the nucleotides. Alternatively, substantial homology exists when the segments will hybridize under selective hybridization conditions, to the complement of the strand. The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley-Interscience, New York (1987).

The nucleic acid compositions of the present invention, while often in a native sequence (except for modified restriction sites and the like), from either cDNA, genomic or mixtures may be mutated, thereof in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame.

Transgenic Nonhuman Animals Capable of Producing Heterologous Antibodies

As has been discussed supra, it is desirable to produce human immunoglobulins that are reactive with specific human antigens that are promising therapeutic and/or diagnostic targets. However, producing human immunoglobulins that bind specifically with human antigens is problematic.

First, the immunized animal that serves as the source of B cells must make an immune response against the presented antigen. In order for an animal to make an immune response, the antigen presented must be foreign and the animal must not be tolerant to the antigen. Thus, for example, if it is desired to produce a human monoclonal antibody with an idiotype that binds to a human protein, self-tolerance will prevent an immunized human from making a substantial immune response to the human protein, since the only epitopes of the antigen that may be immunogenic will be those that result from polymorphism of the protein within the human population (allogeneic epitopes).

Second, if the animal that serves as the source of B-cells for forming a hybridoma (a human in the illustrative given example) does make an immune response against an authentic self antigen, a severe autoimmune disease may result in the animal. Where humans would be used as a source of B-cells for a hybridoma, such autoimmunization would be considered unethical by contemporary standards. Thus, developing hybridomas secreting human immunoglobulin chains specifically reactive with predetermined human antigens is problematic, since a reliable source of human antibody-secreting B cells that can evoke an antibody response against predetermined human antigens is needed.

Examples of mice capable of overcoming these issues include the transgenic and transchromosomic mice referred to herein as the HuMAb Mouse® and KM Mouse®, respectively, and are collectively referred to herein as "human Ig mice."

The HuMAb Mouse® (Medarex®, Inc.) contains human immunoglobulin gene miniloci that encode unrearranged human heavy (μ and γ) and κ light chain immunoglobulin sequences, together with targeted mutations that inactivate the endogenous μ and κ chain loci (see e.g., Lonberg, et al. (1994) Nature 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal antibodies (Lonberg, N. et al. (1994), supra; reviewed in Lonberg, N. (1994) Handbook of Experimental Pharmacology 113:49-101; Lonberg, N. and Huszar, D. (1995) Intern. Rev. Immunol. 13: 65-93, and Harding, F. and Lonberg, N. (1995) Ann. N.Y. Acad. Sci. 764:536-546). Preparation and use of the HuMAb Mouse®, and the genomic modifications carried by such mice, is further described in Taylor, L. et al. (1992) Nucleic Acids Research 20:6287-6295; Chen, J. et al. (1993) International Immunology 5: 647-656; Tuaillon et al. (1993) Proc. Natl. Acad. Sci. USA 90:3720-3724; Choi et al. (1993) Nature Genetics 4:117-123; Chen, J. et al. (1993) EMBO J. 12: 82**30; Tuaillon et al. (1994) J. Immunol. 152:2912-2920; Taylor, L. et al. (1994) International Immunology 6: 579-591; and Fishwild, D. et al. (1996) Nature Biotechnology 14: 845-851, the contents of all of which are hereby specifically incorporated by reference in their entirety. See further, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al., each of which is also incorporated by reference.

In another embodiment, human antibodies can be raised using a mouse that carries human immunoglobulin sequences on transgenes and transchomosomes, such as a mouse that carries a human heavy chain transgene and a human light chain transchromosome. This mouse is referred to herein as a "KM Mouse®," and is described in detail in PCT Publication WO 02/43478 to Ishida et al.

Still further, alternative transgenic animal systems expressing human immunoglobulin genes are available in the art. For example, an alternative transgenic system referred to as the Xenomouse (Amgen, Inc.) can be used; such mice are described in, for example, U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise antibodies to the target of choice. For example, mice carrying both a human heavy chain transchromosome and a human light chain tranchromosome, referred to as "TC mice" can be used; such mice are described in Tomizuka et al. (2000) Proc. Natl. Acad. Sci. USA 97:722-727. Furthermore, cows carrying human heavy and light chain transchromosomes have been described in the art (Kuroiwa et al. (2002) Nature Biotechnology 20:889-894) and PCT application No. WO/2002/092812 and can be used to raise antibodies of the invention.

Human monoclonal antibodies can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

The design of a transgenic non-human animal that responds to foreign antigen stimulation with a heterologous antibody repertoire, requires that the heterologous immunoglobulin transgenes contained within the transgenic animal function correctly throughout the pathway of B-cell development. Accordingly, the transgenes of the invention are constructed so as to produce one or more of the following: (1) high level and cell-type specific expression, (2) functional gene rearrangement, (3) activation of and response to allelic exclusion, (4) expression of a sufficient primary repertoire, (5) signal transduction, (6) somatic hypermutation, and (7) domination of the transgene antibody locus during the immune response.

As will be apparent from the following disclosure, not all of the foregoing criteria need be met. For example, in those embodiments wherein the endogenous immunoglobulin loci of the transgenic animal are functionally disrupted, the transgene need not activate allelic exclusion. Further, in those embodiments wherein the transgene comprises a functionally rearranged heavy and/or light chain immunoglobulin gene, the second criteria of functional gene rearrangement is unnecessary, at least for that transgene which is already rearranged. For background on molecular immunology, see, Fundamental Immunology, 5nd edition (2003), Paul William E., ed. Lippincott Williams & Wilkins, P. A., which is incorporated herein by reference.

The transgenes of the invention include a heavy chain transgene comprising DNA encoding at least one variable gene segment, one diversity gene segment, one joining gene segment and at least one constant region gene segment. The immunoglobulin light chain transgene comprises DNA encoding at least one variable gene segment, one joining gene segment and at least one constant region gene segment. The gene segments encoding the light and heavy chain gene segments are heterologous to the transgenic non-human animal in that they are derived from, or correspond to, DNA encoding immunoglobulin heavy and light chain gene segments from a species not consisting of the transgenic non-human animal. In one aspect of the invention, the transgene is constructed such that the individual gene segments are unrearranged, i.e., not rearranged so as to encode a functional immunoglobulin light or heavy chain. Such unrearranged transgenes support recombination of the V, D, and J gene segments (functional rearrangement) and preferably support incorporation of all or a portion of a D region gene segment in the resultant rearranged immunoglobulin heavy chain within the transgenic non-human animal when exposed to antigen.

In an alternate embodiment, the transgenes comprise an unrearranged "mini-locus." Such transgenes typically comprise a substantial portion of the C, D, and J segments as well as a subset of the V gene segments. In such transgene constructs, the various regulatory sequences, e.g. promoters, enhancers, class switch regions, splice-donor and splice-acceptor sequences for RNA processing, recombination signals and the like, comprise corresponding sequences derived from the heterologous DNA. Such regulatory sequences may be incorporated into the transgene from the same or a related species of the non-human animal used in the invention. For example, human immunoglobulin gene segments may be combined in a transgene with a rodent immunoglobulin enhancer sequence for use in a transgenic mouse. Alternatively, synthetic regulatory sequences may be incorporated into the transgene, wherein such synthetic regulatory sequences are not homologous to a functional DNA sequence that is known to occur naturally in the genomes of mammals. Synthetic regulatory sequences are designed according to consensus rules, such as, for example, those specifying the permissible sequences of a splice-acceptor site or a promoter/enhancer motif. For example, a minilocus comprises a portion of the genomic immunoglobulin locus having at least one internal (i.e., not at a terminus of the portion) deletion of a non-essential DNA portion (e.g., intervening sequence; intron or portion thereof) as compared to the naturally-occurring germline Ig locus.

The invention also includes transgenic animals containing germ line cells having a heavy and light transgene wherein one of the said transgenes contains rearranged gene segments with the other containing unrearranged gene segments. In the preferred embodiments, the rearranged transgene is a light chain immunoglobulin transgene and the unrearranged transgene is a heavy chain immunoglobulin transgene.

The Structure and Generation of Antibodies

The basic structure of all immunoglobulins is based upon a unit consisting of two light polypeptide chains and two heavy polypeptide chains. Each light chain comprises two regions known as the variable light chain region and the constant light chain region. Similarly, the immunoglobulin heavy chain comprises two regions designated the variable heavy chain region and the constant heavy chain region.

The constant region for the heavy or light chain is encoded by genomic sequences referred to as heavy or light constant region gene ($C_H$) segments. The use of a particular heavy chain gene segment defines the class of immunoglobulin. For example, in humans, the μ constant region gene segments define the IgM class of antibody whereas the use of a γ, γ2, γ3 or γ4 constant region gene segment defines the IgG class of antibodies as well as the IgG subclasses IgG1 through IgG4. Similarly, the use of a $\alpha_1$ or $\alpha_2$ constant region gene segment defines the IgA class of antibodies as well as the subclasses IgA1 and IgA2. The δ and ε constant region gene segments define the IgD and IgE antibody classes, respectively.

The variable regions of the heavy and light immunoglobulin chains together contain the antigen binding domain of the antibody. Because of the need for diversity in this region of the antibody to permit binding to a wide range of antigens, the DNA encoding the initial or primary repertoire variable region comprises a number of different DNA segments derived from families of specific variable region gene segments. In the case of the light chain variable region, such families comprise variable (V) gene segments and joining (J) gene segments. Thus, the initial variable region of the light chain is encoded by one V gene segment and one J gene segment each selected from the family of V and J gene segments contained in the genomic DNA of the organism. In the case of the heavy chain variable region, the DNA encoding the initial or primary repertoire variable region of the heavy chain comprises one heavy chain V gene segment, one heavy chain diversity (D) gene segment and one J gene segment, each selected from the appropriate V, D and J families of immunoglobulin gene segments in genomic DNA.

In order to increase the diversity of sequences that contribute to forming antibody binding sites, it is preferable that a heavy chain transgene include cis-acting sequences that support functional V-D-J rearrangement that can incorporate all or part of a D region gene sequence in a rearranged V-D-J gene sequence. Typically, at least about 1 percent of expressed transgene-encoded heavy chains (or mRNAs)

include recognizable D region sequences in the V region. Preferably, at least about 10 percent of transgene-encoded V regions include recognizable D region sequences, more preferably at least about 30 percent, and most preferably more than 50 percent include recognizable D region sequences.

A recognizable D region sequence is generally at least about eight consecutive nucleotides corresponding to a sequence present in a D region gene segment of a heavy chain transgene and/or the amino acid sequence encoded by such D region nucleotide sequence. For example, if a transgene includes the D region gene DHQ52, a transgene-encoded mRNA containing the sequence 5'-CTAACTGGGGA-3' (SEQ ID NO:1) located in the V region between a V gene segment sequence and a J gene segment sequence is recognizable as containing a D region sequence, specifically a DHQ52 sequence. Similarly, for example, if a transgene includes the D region gene DHQ52, a transgene-encoded heavy chain polypeptide containing the amino acid sequence -LTG- located in the V region between a V gene segment amino acid sequence and a J gene segment amino acid sequence may be recognizable as containing a D region sequence, specifically a DHQ52 sequence. However, since D region segments may be incorporated in VDJ joining to various extents and in various reading frames, a comparison of the D region area of a heavy chain variable region to the D region segments present in the transgene is necessary to determine the incorporation of particular D segments. Moreover, potential exonuclease digestion during recombination may lead to imprecise V-D and D-J joints during V-D-J recombination.

However, because of somatic mutation and N-region addition, some D region sequences may be recognizable but may not correspond identically to a consecutive D region sequence in the transgene. For example, a nucleotide sequence 5'-CTAAXTGGGGA-3' (SEQ ID NO:2), where X is A, T, or G, and which is located in a heavy chain V region and flanked by a V region gene sequence and a J region gene sequence, can be recognized as corresponding to the DHQ52 sequence 5'-CTAACTGGGA-3' (SEQ ID NO:3). Similarly, for example, the polypeptide sequences -LNG-, -LIG-, -LSG-, -KWG-, or -NWG- located in a V region and flanked on the amino-terminal side by an amino acid sequence encoded by a transgene V gene sequence and flanked on the carboxyterminal side by an amino acid sequence encoded by a transgene J gene sequence is recognizable as a D region sequence.

Therefore, because somatic mutation and N-region addition can produce mutations in sequences derived from a transgene D region, the following definition is provided as a guide for determining the presence of a recognizable D region sequence. An amino acid sequence or nucleotide sequence is recognizable as a D region sequence if: (1) the sequence is located in a V region and is flanked on one side by a V gene sequence (nucleotide sequence or deduced amino acid sequence) and on the other side by a J gene sequence (nucleotide sequence or deduced amino acid sequence) and (2) the sequence is substantially identical or substantially similar to a known D gene sequence (nucleotide sequence or encoded amino acid sequence).

The term "substantial identity" as used herein denotes a characteristic of a polypeptide sequence or nucleic acid sequence, wherein the polypeptide sequence has at least 50 percent sequence identity compared to a reference sequence, often at least about 80% sequence identity and sometimes more than about 90% sequence identity, and the nucleic acid sequence has at least 70 percent sequence identity compared to a reference sequence. The percentage of sequence identity is calculated excluding small deletions or additions which total less than 35 percent of the reference sequence. The reference sequence may be a subset of a larger sequence, such as an entire D gene; however, the reference sequence is at least 8 nucleotides long in the case of polynucleotides, and at least 3 amino residues long in the case of a polypeptide. Typically, the reference sequence is at least 8 to 12 nucleotides or at least 3 to 4 amino acids, and preferably the reference sequence is 12 to 15 nucleotides or more, or at least 5 amino acids.

The term "substantial similarity" denotes a characteristic of an polypeptide sequence, wherein the polypeptide sequence has at least 80 percent similarity to a reference sequence. The percentage of sequence similarity is calculated by scoring identical amino acids or positional conservative amino acid substitutions as similar. A positional conservative amino acid substitution is one that can result from a single nucleotide substitution; a first amino acid is replaced by a second amino acid where a codon for the first amino acid and a codon for the second amino acid can differ by a single nucleotide substitution. Thus, for example, the sequence -Lys-Glu-Arg-Val- (SEQ ID NO:4) is substantially similar to the sequence -Asn-Asp-Ser-Val- (SEQ ID NO:5), since the codon sequence -AAA-GAA-AGA-GUU- (SEQ ID NO:6) can be mutated to -AAC-GAC-AGC-GUU- (SEQ ID NO:7) by introducing only 3 substitution mutations, single nucleotide substitutions in three of the four original codons. The reference sequence may be a subset of a larger sequence, such as an entire D gene; however, the reference sequence is at least 4 amino residues long. Typically, the reference sequence is at least 5 amino acids, and preferably the reference sequence is 6 amino acids or more.

The Primary Repertoire

The process for generating DNA encoding the heavy and light chain immunoglobulin genes occurs primarily in developing B-cells. Prior to the joining of various immunoglobulin gene segments, the V, D, J and constant (C) gene segments are found, for the most part, in clusters of V, D, J and C gene segments in the precursors of primary repertoire B-cells. Generally, all of the gene segments for a heavy or light chain are located in relatively close proximity on a single chromosome. Such genomic DNA prior to recombination of the various immunoglobulin gene segments is referred to herein as "unrearranged" genomic DNA. During B-cell differentiation, one of each of the appropriate family members of the V, D, J (or only V and J in the case of light chain genes) gene segments are recombined to form functionally rearranged heavy and light immunoglobulin genes. Such functional rearrangement is of the variable region segments to form DNA encoding a functional variable region. This gene segment rearrangement process appears to be sequential. First, heavy chain D-to-J joints are made, followed by heavy chain V-to-DJ joints and light chain V-to-J joints. The DNA encoding this initial form of a functional variable region in a light and/or heavy chain is referred to as "functionally rearranged DNA" or "rearranged DNA". In the case of the heavy chain, such DNA is referred to as "rearranged heavy chain DNA" and in the case of the light chain, such DNA is referred to as "rearranged light chain DNA". Similar language is used to describe the functional rearrangement of the transgenes of the invention.

The recombination of variable region gene segments to form functional heavy and light chain variable regions is mediated by recombination signal sequences (RSS's) that flank recombinationally competent V, D and J segments. RSS's necessary and sufficient to direct recombination, comprise a dyad-symmetric heptamer, an AT-rich nonamer and an intervening spacer region of either 12 or 23 base pairs. These signals are conserved among the different loci and species that carry out D-J (or V-J) recombination and are functionally interchangeable. See Oettinger, et al. (1990), Science, 248, 1517-1523; Cuomo et al. (1994), Nucleic Acids Res., 22(10), 1810-4; Sadofsky, (2001), Nucleic Acids Res., 29(7), 1399-409; all of which are hereby incorporated by reference in their entirety. The heptamer comprises the sequence CACAGTG or its analogue followed by a spacer of unconserved sequence and then a nonamer having the sequence ACAAAAACC or its analogue. These sequences are found on the J, or downstream side, of each V and D gene segment. Immediately preceding the germline D and J segments are again two recombination signal sequences, first the nonamer and then the heptamer again separated by an unconserved sequence. The heptameric and nonameric sequences following a $V_L$, $V_H$ or D segment are complementary to those preceding the $J_L$, D or $J_H$ segments with which they recombine. The spacers between the heptameric and nonameric sequences are either 12 base pairs long or between 22 and 24 base pairs long.

In addition to the rearrangement of V, D and J segments, further diversity is generated in the primary repertoire of immunoglobulin heavy and light chain by way of variable recombination between the V and J segments in the light chain and between the D and J segments of the heavy chain. Such variable recombination is generated by variation in the exact place at which such segments are joined. Such variation in the light chain typically occurs within the last codon of the V gene segment and the first codon of the J segment. Similar imprecision in joining occurs on the heavy chain chromosome between the D and $J_H$ segments and may extend over as many as 10 nucleotides. Furthermore, several nucleotides may be inserted between the D and $J_H$ and between the $V_H$ and D gene segments which are not encoded by genomic DNA. The addition of these nucleotides is known as N-region diversity.

After VJ and/or VDJ rearrangement, transcription of the rearranged variable region and one or more constant region gene segments located downstream from the rearranged variable region produces a primary RNA transcript which upon appropriate RNA splicing results in an mRNA which encodes a full length heavy or light immunoglobulin chain. Such heavy and light chains include a leader signal sequence to effect secretion through and/or insertion of the immunoglobulin into the transmembrane region of the B-cell. The DNA encoding this signal sequence is contained within the first exon of the V segment used to form the variable region of the heavy or light immunoglobulin chain. Appropriate regulatory sequences are also present in the mRNA to control translation of the mRNA to produce the encoded heavy and light immunoglobulin polypeptides which upon proper association with each other form an antibody molecule.

The net effect of such rearrangements in the variable region gene segments and the variable recombination which may occur during such joining, is the production of a primary antibody repertoire. Generally, each B-cell which has differentiated to this stage, produces a single primary repertoire antibody. During this differentiation process, cellular events occur which suppress the functional rearrangement of gene segments other than those contained within the functionally rearranged Ig gene. The process by which diploid B-cells maintain such mono-specificity is termed allelic exclusion.

The Secondary Repertoire

B-cell clones expressing immunoglobulins from within the set of sequences comprising the primary repertoire are immediately available to respond to foreign antigens. Because of the limited diversity generated by simple VJ and VDJ joining, the antibodies produced by the so-called primary response are of relatively low affinity. Two different types of B-cells make up this initial response: precursors of primary antibody-forming cells and precursors of secondary repertoire B-cells (Linton et al., Cell 59:1049-1059 (1989); and Hentges, Clin Exp Immunol. 97 Suppl 1:3-9 (1994) both of which are hereby incorporated by reference in their entirety). The first type of B-cell matures into IgM-secreting plasma cells in response to certain antigens. The other B-cells respond to initial exposure to antigen by entering a T-cell dependent maturation pathway.

During the T-cell dependent maturation of antigen stimulated B-cell clones, the structure of the antibody molecule on the cell surface changes in two ways: the constant region switches to a non-IgM subtype and the sequence of the variable region can be modified by multiple single amino acid substitutions to produce a higher affinity antibody molecule.

As previously indicated, each variable region of a heavy or light Ig chain contains an antigen binding domain. It has been determined by amino acid and nucleic acid sequencing that somatic mutation during the secondary response occurs throughout the V region including the three complementary determining regions (CDR1, CDR2 and CDR3) also referred to as hypervariable regions 1, 2 and 3 (Kabat et al. Sequences of Proteins of Immunological Interest (1991) U.S. Department of Health and Human Services, Washington, D.C., incorporated herein by reference in its entirety). The CDR1 and CDR2 are located within the variable gene segment whereas the CDR3 is largely the result of recombination between V and J gene segments or V, D and J gene segments. Those portions of the variable region which do not consist of CDR1, 2 or 3 are commonly referred to as framework regions designated FR1, FR2, FR3 and FR4. During hypermutation, the rearranged DNA is mutated to give rise to new clones with altered Ig molecules. Those clones with higher affinities for the foreign antigen are selectively expanded by helper T-cells, giving rise to affinity maturation of the expressed antibody. Clonal selection typically results in expression of clones containing new mutation within the CDR1, 2 and/or 3 regions. However, mutations outside these regions also occur which influence the specificity and affinity of the antigen binding domain.

Transgenic Non-Human Animals Capable of Producing Heterologous Antibody

Transgenic non-human animals in one aspect of the invention are produced by introducing at least one of the immunoglobulin transgenes of the invention (discussed hereinafter) into a zygote or early embryo of a non-human animal. The non-human animals which are used in the invention generally comprise any mammal which is capable of rearranging immunoglobulin gene segments to produce a primary antibody response. Such nonhuman transgenic animals may include, for example, transgenic pigs, transgenic rats, transgenic rabbits, transgenic cattle, and other transgenic animal species, particularly mammalian species, known in the art. A particularly preferred non-human animal is the mouse or other members of the rodent family.

However, the invention is not limited to the use of mice. Rather, any non-human mammal which is capable of mounting a primary and secondary antibody response may be used. Such animals include non-human primates, such as chimpanzee, bovine, ovine, and porcine species, other members of the rodent family, e.g. rat, as well as rabbit and guinea pig. Particular preferred animals are mouse, rat, rabbit and guinea pig, most preferably mouse.

In one embodiment of the invention, various gene segments from the human genome are used in heavy and light chain transgenes in an unrearranged form. In this embodiment, such transgenes are introduced into mice. The unrearranged gene segments of the light and/or heavy chain transgene have DNA sequences unique to the human species which are distinguishable from the endogenous immunoglobulin gene segments in the mouse genome. They may be readily detected in unrearranged form in the germ line and somatic cells not consisting of B-cells and in rearranged form in B-cells.

In an alternate embodiment of the invention, the transgenes comprise rearranged heavy and/or light immunoglobulin transgenes. Specific segments of such transgenes corresponding to functionally rearranged VDJ or VJ segments, contain immunoglobulin DNA sequences which are also clearly distinguishable from the endogenous immunoglobulin gene segments in the mouse.

Such differences in DNA sequence are also reflected in the amino acid sequence encoded by such human immunoglobulin transgenes as compared to those encoded by mouse B-cells. Thus, human immunoglobulin amino acid sequences may be detected in the transgenic non-human animals of the invention with antibodies specific for immunoglobulin epitopes encoded by human immunoglobulin gene segments.

Transgenic B-cells containing unrearranged transgenes from human or other species functionally recombine the appropriate gene segments to form functionally rearranged light and heavy chain variable regions. It will be readily apparent that the antibody encoded by such rearranged transgenes has a DNA and/or amino acid sequence which is heterologous to that normally encountered in the nonhuman animal used to practice the invention.

Unrearranged Transgenes

As used herein, an "unrearranged immunoglobulin heavy chain transgene" comprises DNA encoding at least one variable gene segment, one diversity gene segment, one joining gene segment and one constant region gene segment. Each of the gene segments of said heavy chain transgene are derived from, or has a sequence corresponding to, DNA encoding immunoglobulin heavy chain gene segments from a species not consisting of the non-human animal into which said transgene is introduced. Similarly, as used herein, an "unrearranged immunoglobulin light chain transgene" comprises DNA encoding at least one variable gene segment, one joining gene segment and at least one constant region gene segment wherein each gene segment of said light chain transgene is derived from, or has a sequence corresponding to, DNA encoding immunoglobulin light chain gene segments from a species not consisting of the non-human animal into which said light chain transgene is introduced.

Such heavy and light chain transgenes in this aspect of the invention contain the above-identified gene segments in an unrearranged form. Thus, interposed between the V, D and J segments in the heavy chain transgene and between the V and J segments on the light chain transgene are appropriate recombination signal sequences (RSS's). In addition, such transgenes also include appropriate RNA splicing signals to join a constant region gene segment with the VJ or VDJ rearranged variable region.

In order to facilitate isotype switching within a heavy chain transgene containing more than one C region gene segment, e.g. Cμ and Cγ1 from the human genome, as explained below "switch regions" are incorporated upstream from each of the constant region gene segments and downstream from the variable region gene segments to permit recombination between such constant regions to allow for immunoglobulin class switching, e.g. from IgM to IgG. Such heavy and light immunoglobulin transgenes also contain transcription control sequences including promoter regions situated upstream from the variable region gene segments which typically contain TATA motifs. A promoter region can be defined approximately as a DNA sequence that, when operably linked to a downstream sequence, can produce transcription of the downstream sequence. Promoters may require the presence of additional linked cis-acting sequences in order to produce efficient transcription. In addition, other sequences that participate in the transcription of sterile transcripts are preferably included. Examples of sequences that participate in expression of sterile transcripts can be found in the published literature, including Rothman et al., Intl. Immunol. 2:621-627 (1990); Reid et al., Proc. Natl. Acad. Sci. USA 86:840-844 (1989); Stavnezer et al., Proc. Natl. Acad. Sci. USA 85:7704-7708 (1988); and Mills et al., Nucl. Acids Res. 18:7305-7316 (1991), each of which is incorporated herein by reference. These sequences typically include about at least 50 bp immediately upstream of a switch region, preferably about at least 200 bp upstream of a switch region; and more preferably about at least 200-1000 bp or more upstream of a switch region. Suitable sequences occur immediately upstream of the human $S_\gamma 1$, $S_\gamma 2$, $S_\gamma 3$, $S_\gamma 4$, $S_\alpha 1$, $S_\alpha 2$, and $S_\epsilon$ switch regions; the sequences immediately upstream of the human $S_\gamma 1$, and $S_\gamma 3$ switch regions can be used to advantage, with $S_\gamma 1$ generally preferred. Alternatively, or in combination, murine Ig switch sequences may be used; it may frequently be advantageous to employ Ig switch sequences of the same species as the transgenic non-human animal. Furthermore, interferon (IFN) inducible transcriptional regulatory elements, such as IFN-inducible enhancers, are preferably included immediately upstream of transgene switch sequences.

In addition to promoters, other regulatory sequences which function primarily in B-lineage cells are used. Thus, for example, a light chain enhancer sequence situated preferably between the J and constant region gene segments on the light chain transgene is used to enhance transgene expression, thereby facilitating allelic exclusion. In the case of the heavy chain transgene, regulatory enhancers and also employed. Such regulatory sequences are used to maximize the transcription and translation of the transgene so as to induce allelic exclusion and to provide relatively high levels of transgene expression.

Although the foregoing promoter and enhancer regulatory control sequences have been generically described, such regulatory sequences may be heterologous to the nonhuman animal being derived from the genomic DNA from which the heterologous transgene immunoglobulin gene segments are obtained. Alternately, such regulatory gene segments are derived from the corresponding regulatory sequences in the genome of the non-human animal, or closely related species, which contains the heavy and light transgene.

In the preferred embodiments, gene segments are derived from human beings. The transgenic non-human animals harboring such heavy and light transgenes are capable of mounting an Ig-mediated immune response to a specific antigen administered to such an animal. B-cells are produced within such an animal which are capable of producing heterologous human antibody. After immortalization, and the selection for an appropriate monoclonal antibody (Mab), e.g. a hybridoma, a source of therapeutic human monoclonal antibody is provided. Such human Mabs have significantly reduced immunogenicity when therapeutically administered to humans.

Although the preferred embodiments disclose the construction of heavy and light transgenes containing human gene segments, the invention is not so limited. In this regard, it is to be understood that the teachings described herein may be readily adapted to utilize immunoglobulin gene segments from a species other than human beings. For example, in addition to the therapeutic treatment of humans with the antibodies of the invention, therapeutic antibodies encoded by appropriate gene segments may be utilized to generate monoclonal antibodies for use in the veterinary sciences.

Monoclonal Antibodies

Monoclonal antibodies can be obtained by various techniques familiar to those skilled in the art. Briefly, spleen cells from an animal immunized with a desired antigen are immortalized, commonly by fusion with a myeloma cell (see, Kohler and Milstein, Eur. J. Immunol., 6:511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Various techniques useful in these arts are discussed, for example, in Harlow and Lane, Using Antibodies: A Laboratory Manual, Cold spring Harbor, N.Y. (1998), which is hereby incorporated by reference in its entirety, including: immunization of animals to produce immunoglobulins; production of monoclonal antibodies; labeling immunoglobulins for use as probes; immunoaffinity purification; and immunoassays.

The Transgenic Primary Repertoire

A. The Human Immunoglobulin Loci

An important requirement for transgene function is the generation of a primary antibody repertoire that is diverse enough to trigger a secondary immune response for a wide range of antigens. The rearranged heavy chain gene consists of a signal peptide exon, a variable region exon and a tandem array of multi-domain constant region regions, each of which is encoded by several exons. Each of the constant region genes encode the constant portion of a different class of immunoglobulins. During B-cell development, V region proximal constant regions are deleted leading to the expression of new heavy chain classes. For each heavy chain class, alternative patterns of RNA splicing give rise to both transmembrane and secreted immunoglobulins.

The human heavy chain locus is estimated to consist of approximately 200 V gene segments (current data supports the existence of about 50-100 V gene segments) spanning 2 Mb, approximately 30 D gene segments spanning about 40 kb, six J segments clustered within a 3 kb span, and nine constant region gene segments spread out over approximately 300 kb. The entire locus spans approximately 2.5 Mb of the distal portion of the long arm of chromosome 14.

B. Gene Fragment Transgenes

1. Heavy Chain Transgene

In a preferred embodiment, immunoglobulin heavy and light chain transgenes comprise unrearranged genomic DNA from humans. In the case of the heavy chain, a preferred transgene comprises a NotI fragment having a length between 670 to 830 kb. This fragment contains members of all six of the known $V_H$ families, the D and J gene segments, as well as the μ, δ, γ3, γ1 and α1 constant regions (Berman et al., EMBO J. 7:727-738 (1988), which is incorporated herein by reference). A transgenic mouse line containing this transgene correctly expresses a heavy chain class required for B-cell development (IgM) and at least one switched heavy chain class ($IgG_1$), in conjunction with a sufficiently large repertoire of variable regions to trigger a secondary response for most antigens.

As discussed in detail in the section entitled "Preferred Embodiments," preferred transgenes comprising heavy gene sequences include, but are not limited to, the inserts of pHC2, pGP69-7 VHC, pVx6, VDJCE, V12DJCE, CTD-3054M17, BAC fusion #1, BAC fusion #2, BAC fusion #3, BAC fusion #4, BAC fusion #5, yIgH24a, yIgH10, and pIgYBac.

2. Light Chain Transgene

A genomic fragment containing all of the necessary gene segments and regulatory sequences from a human light chain locus may be similarly constructed. Such transgenes are constructed as described in the Examples and in U.S. Pat. No. 5,789,650, entitled "Transgenic Non-Human Animals Capable of Producing Heterologous Antibodies."

C. Minilocus Transgenes

As used herein, the term "immunoglobulin minilocus" refers to a DNA sequence (which may be within a longer sequence), usually of less than about 150 kb, typically between about 25 and 100 kb, containing at least one each of the following: a functional variable (V) gene segment, a functional joining (J) region segment, at least one functional constant (C) region gene segment, and—if it is a heavy chain minilocus—a functional diversity (D) region segment, such that said DNA sequence contains at least one substantial discontinuity (e.g., a deletion, usually of at least about 2 to 5 kb, preferably 10-25 kb or more, relative to the homologous genomic DNA sequence). A light chain minilocus transgene will be at least 25 kb in length, typically 50 to 60 kb. A heavy chain transgene will typically be about 70 to 80 kb in length, preferably at least about 60 kb with two constant regions operably linked to switch regions. Furthermore, the individual elements of the minilocus are preferably in the germline configuration and capable of undergoing gene rearrangement in the pre-B cell of a transgenic animal so as to express functional antibody molecules with diverse antigen specificities encoded entirely by the elements of the minilocus. Further, a heavy chain minilocus comprising at least two $C_H$ genes and the requisite switching sequences is typically capable of undergoing isotype switching, so that functional antibody molecules of different immunoglobulin classes will be generated. Such isotype switching may occur in vivo in B-cells residing within the transgenic nonhuman animal, or may occur in cultured cells of the B-cell lineage which have been explanted from the transgenic nonhuman animal.

In an alternate preferred embodiment, immunoglobulin heavy chain transgenes comprise one or more of each of the $V_H$, D, and $J_H$ gene segments and two or more of the $C_H$ genes. At least one of each appropriate type gene segment is incorporated into the minilocus transgene. With regard to the $C_H$ segments for the heavy chain transgene, it is preferred that the transgene contain at least one μ gene segment and at least one other constant region gene segment, more preferably a γ gene segment, and most preferably γ3 or γ1. This preference is to allow for class switching between IgM and IgG forms of the encoded immunoglobulin and the production of a secretable form of high affinity non-IgM immunoglobulin. Other constant region gene segments may also be used such as those which encode for the production of IgD, IgA and IgE.

Those skilled in the art will also construct transgenes wherein the order of occurrence of heavy chain $C_H$ genes will be different from the naturally-occurring spatial order found in the germline of the species serving as the donor of the $C_H$ genes.

Additionally, those skilled in the art can select $C_H$ genes from more than one individual of a species (e.g., allogeneic $C_H$ genes) and incorporate said genes in the transgene as supernumerary $C_H$ genes capable of undergoing isotype switching; the resultant transgenic nonhuman animal may then, in some embodiments, make antibodies of various classes including all of the allotypes represented in the species from which the transgene $C_H$ genes were obtained.

Still further, those skilled in the art can select $C_H$ genes from different species to incorporate into the transgene. Functional switch sequences are included with each $C_H$ gene, although the switch sequences used are not necessarily those which occur naturally adjacent to the $C_H$ gene. Interspecies $C_H$ gene combinations will produce a transgenic nonhuman animal which may produce antibodies of various classes corresponding to $C_H$ genes from various species. Transgenic nonhuman animals containing interspecies $C_H$ transgenes may serve as the source of B-cells for constructing hybridomas to produce monoclonals for veterinary uses.

The heavy chain J region segments in the human comprise six functional J segments and three pseudo genes clustered in a 3 kb stretch of DNA. Given its relatively compact size and the ability to isolate these segments together with the μ gene and the 5' portion of the δ gene on a single 23 kb SFiI/SpeI fragment (Sado et al., Biochem. Biophys. Res. Comm. 154:264271 (1988), which is incorporated herein by reference), it is preferred that all of the J region gene segments be used in the mini-locus construct. Since this fragment spans the region between the μ and δ genes, it is likely to contain all of the 3' cis-linked regulatory elements required for μ expression. Furthermore, because this fragment includes the entire J region, it contains the heavy chain enhancer and the p switch region (Mills et al., Nature 306:809 (1983); Yancopoulos and Alt, Ann. Rev. Immunol. 4:339-368 (1986), which are incorporated herein by reference). It also contains the transcription start sites which trigger VDJ joining to form primary repertoire B-cells (Yancopoulos and Alt, Cell 40:271-281 (1985), which is incorporated herein by reference). Alternatively, a 36 kb BssHII/SpeI1 fragment, which includes part on the D region, may be used in place of the 23 kb SfiI/SpeI1 fragment. The use of such a fragment increases the amount of 5' flanking sequence to facilitate efficient D-to-J joining.

The human D region consists of 4 homologous 9 kb subregions, linked in tandem (Siebenlist, et al. (1981), Nature, 294, 631-635). Each subregion contains up to 10 individual D segments. Two different strategies are used to generate a mini-locus D region. The first strategy involves using only those D segments located in a short contiguous stretch of DNA that includes one or two of the repeated D subregions. A candidate is a single 15 kb fragment that contains 12 individual D segments. This piece of DNA consists of 2 contiguous EcoRI fragments and has been completely sequenced (Ichihara, et al. (1988), EMBO J., 7, 4141-4150). Twelve D segments should be sufficient for a primary repertoire. However, given the dispersed nature of the D region, an alternative strategy is to ligate together several non-contiguous D-segment containing fragments, to produce a smaller piece of DNA with a greater number of segments. Additional D-segment genes can be identified, for example, by the presence of characteristic flanking nonamer and heptamer sequences, supra, and by reference to the literature.

At least one, and preferably more than one V gene segment is used to construct the heavy chain minilocus transgene. Rearranged or unrearranged V segments, D segments, J segments, and C genes, with or without flanking sequences, can be isolated as described in U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al., each of which is also incorporated by reference.

A minilocus light chain transgene may be similarly constructed from the human λ or κ immunoglobulin locus. Thus, for example, an immunoglobulin heavy chain minilocus transgene construct, e.g., of about 75 kb, encoding V, D, J and constant region sequences can be formed from a plurality of DNA fragments, with each sequence being substantially homologous to human gene sequences. Preferably, the sequences are operably linked to transcription regulatory sequences and are capable of undergoing rearrangement. With two or more appropriately placed constant region sequences (e.g., μ and γ) and switch regions, switch recombination also occurs. An exemplary light chain transgene construct can be formed similarly from a plurality of DNA fragments, substantially homologous to human DNA and capable of undergoing rearrangement, as described in U.S. Pat. Nos. 5,545,806; 5,569,825; 5,625,126; 5,633,425; 5,789,650; 5,877,397; 5,661,016; 5,814,318; 5,874,299; and 5,770,429.

D. Functional Disruption of Endogenous Immunoglobulin Loci

The expression of successfully rearranged immunoglobulin heavy and light transgenes is expected to have a dominant effect by suppressing the rearrangement of the endogenous immunoglobulin genes in the transgenic nonhuman animal. However, another way to generate a nonhuman that is devoid of endogenous antibodies is by mutating the endogenous immunoglobulin loci. Using embryonic stem cell technology and homologous recombination, the endogenous immunoglobulin repertoire can be readily eliminated. The following describes the functional description of the mouse immunoglobulin loci. The vectors and methods disclosed, however, can be readily adapted for use in other non-human animals.

Briefly, this technology involves the inactivation of a gene, by homologous recombination, in a pluripotent cell line that is capable of differentiating into germ cell tissue. A DNA construct that contains an altered, copy of a mouse immunoglobulin gene is introduced into the nuclei of embryonic stem cells. In a portion of the cells, the introduced DNA recombines with the endogenous copy of the mouse gene, replacing it with the altered copy. Cells containing the newly engineered genetic lesion are injected into a host mouse embryo, which is reimplanted into a recipient female. Some of these embryos develop into chimeric mice that possess germ cells entirely derived from the mutant cell line. Therefore, by breeding the chimeric mice it is possible to obtain a new line of mice containing the introduced genetic lesion (reviewed by Capecchi (1989), Science, 244, 1288-1292).

Because the mouse λ locus contributes to only 5% of the immunoglobulins, inactivation of the heavy chain and/or κ-light chain loci is sufficient. There are three ways to disrupt each of these loci, deletion of the J region, deletion of the J-C intron enhancer, and disruption of constant region coding sequences by the introduction of a stop codon. The last option is the most straightforward, in terms of DNA construct design. Elimination of the μ gene disrupts B-cell maturation thereby preventing class switching to any of the functional heavy chain segments. The strategy for knocking out these loci is outlined below.

To disrupt the mouse μ and κ genes, targeting vectors are used based on the design employed by Jaenisch and co-workers (Zijlstra, et al. (1989), Nature, 342, 435-438) for the successful disruption of the mouse β2-microglobulin gene. The neomycin resistance gene (neo), from the plasmid pMCIneo is inserted into the coding region of the target gene. The pMCIneo insert uses a hybrid viral promoter/enhancer sequence to drive neo expression. This promoter is active in embryonic stem cells. Therefore, neo can be used as a selectable marker for integration of the knock-out construct. The HSV thymidine kinase (tk) gene is added to the end of the construct as a negative selection marker against random insertion events (Zijlstra, et al., supra.).

A preferred strategy for disrupting the heavy chain locus is the elimination of the J region. This region is fairly compact in the mouse, spanning only 1.3 kb. To construct a gene targeting vector, a 15 kb KpnI fragment containing all of the secreted IgA constant region exons from mouse genomic library is isolated. The 1.3 kb J region is replaced with the 1.1 kb insert from pMCIneo. The HSV tk gene is then added to the 5' end of the KpnI fragment. Correct integration of this construct, via homologous recombination, will result in the replacement of the mouse $J_H$ region with the neo gene. Recombinants are screened by PCR, using a primer based on the neo gene and a primer homologous to mouse sequences 5' of the KpnI site in the D region.

Alternatively, the heavy-chain locus is knocked out by disrupting the coding region of the μ gene. This approach involves the same 15 kb KpnI fragment used in the previous approach. The 1.1 kb insert from pMCIneo is inserted at a unique BamHI site in exon II, and the HSV tk gene added to the 3' KpnI end. Double crossover events on either side of the neo insert, that eliminate the tk gene, are then selected for. These are detected from pools of selected clones by PCR amplification. One of the PCR primers is derived from neo sequences and the other from mouse sequences outside of the targeting vector.

E. Suppressing Expression of Endogenous Immunoglobulin Loci

In addition to functional disruption of endogenous Ig loci, an alternative method for preventing the expression of an endogenous Ig locus is suppression. Suppression of endogenous Ig genes may be accomplished with antisense RNA produced from one or more integrated transgenes, by antisense oligonucleotides, and/or by administration of antisera specific for one or more endogenous Ig chains.

Antisense Polynucleotides

Antisense RNA transgenes can be employed to partially or totally knock-out expression of specific genes (Juliano et al., J Cell Biol., 169(6):847-57 (2005); Antisense Research and Application, (2002). S. T. Crooke, Ed., Springer, N.Y.; Pepin et al. (1991) Nature 355: 725; Helene., C. and Toulme, J. (1990) Biochimica Biophys. Acta 1049: 99; Stout, J. and Caskey, T. (1990) Somat. Cell Mol. Genet. 16: 369; Munir et al. (1990) Somat. Cell Mol. Genet. 16: 383, each of which is incorporated herein by reference).

"Antisense polynucleotides" are polynucleotides that: (1) are complementary to all or part of a reference sequence, such as a sequence of an endogenous Ig $C_H$ or $C_L$ region, and (2) which specifically hybridize to a complementary target sequence, such as a chromosomal gene locus or a Ig MRNA. Such complementary antisense polynucleotides may include nucleotide substitutions, additions, deletions, or transpositions, so long as specific hybridization to the relevant target sequence is retained as a functional property of the polynucleotide. Complementary antisense polynucleotides include soluble antisense RNA or DNA oligonucleotides which can hybridize specifically to individual mRNA species and prevent transcription and/or RNA processing of the mRNA species and/or translation of the encoded polypeptide (Juliano et al., J Cell Biol., 169(6):847-57 (2005); Ching et al., Proc. Natl. Acad. Sci. U.S.A. 86:10006-10010 (1989); Broder et al., Ann. Int. Med. 113:604-618 (1990); Loreau et al., FEBS Letters 274:53-56 (1990); Holcenberg et al., WO91/11535; U.S. Ser. No. 07/530,165 ("New human CRIPTO gene"); WO91/09865; WO91/04753; WO90/13641; and EP 386563, each of which is incorporated herein by reference). An antisense sequence is a polynucleotide sequence that is complementary to at least one immunoglobulin gene sequence of at least about 15 contiguous nucleotides in length, typically at least 20 to 30 nucleotides in length, and preferably more than about 30 nucleotides in length. However, in some embodiments, antisense sequences may have substitutions, additions, or deletions as compared to the complementary immunoglobulin gene sequence, so long as specific hybridization is retained as a property of the antisense polynucleotide. Generally, an antisense sequence is complementary to an endogenous immunoglobulin gene sequence that encodes, or has the potential to encode after DNA rearrangement, an immunoglobulin chain. In some cases, sense sequences corresponding to an immunoglobulin gene sequence may function to suppress expression, particularly by interfering with transcription.

The antisense polynucleotides therefore inhibit production of the encoded polypeptide(s). In this regard, antisense polynucleotides that inhibit transcription and/or translation of one or more endogenous Ig loci can alter the capacity and/or specificity of a non-human animal to produce immunoglobulin chains encoded by endogenous Ig loci.

Antisense polynucleotides may be produced from a heterologous expression cassette in a transfectant cell or transgenic cell, such as a transgenic pluripotent hematopoietic stem cell used to reconstitute all or part of the hematopoietic stem cell population of an individual, or a transgenic non-human animal. Alternatively, the antisense polynucleotides may comprise soluble oligonucleotides that are administered to the external milieu, either in culture medium in vitro or in the circulatory system or interstitial fluid in vivo. Soluble antisense polynucleotides present in the external milieu have been shown to gain access to the cytoplasm and inhibit translation of specific mRNA species. In some embodiments the antisense polynucleotides comprise methylphosphonate moieties, alternatively phosphorothiolates or O-methylribonucleotides may be used, and chimeric oligonucleotides may also be used (Juliano et al., J Cell Biol., 169(6):847-57 (2005); Dagle et al. (1990) Nucleic Acids Res. 18: 4751). For some applications, antisense oligonucleotides may comprise polyamide nucleic acids (Nielsen et al. (1991) Science 254: 1497). For general methods relating to antisense polynucleotides, see Antisense Research and Application, (2002). S. T. Crooke, Ed., Springer, N.Y., and Antisense RNA and DNA, (1988), D. A. Melton, Ed., Cold Spring Harbor Laboratory, Cold Spring Harbor, N.Y., both of which are hereby incorporated by reference in their entirety).

Antisense polynucleotides complementary to one or more sequences are employed to inhibit transcription, RNA processing, and/or translation of the cognate mRNA species and thereby effect a reduction in the amount of the respective encoded polypeptide. Such antisense polynucleotides can provide a therapeutic function by inhibiting the formation of one or more endogenous Ig chains in vivo.

Whether as soluble antisense oligonucleotides or as antisense RNA transcribed from an antisense transgene, the antisense polynucleotides of this invention are selected so as to hybridize preferentially to endogenous Ig sequences at physiological conditions in vivo. Most typically, the selected antisense polynucleotides will not appreciably hybridize to heterologous Ig sequences encoded by a heavy or light chain transgene of the invention (i.e., the antisense oligonucleotides will not inhibit transgene Ig expression by more than about 25 to 35 percent).

Antiserum Suppression

Partial or complete suppression of endogenous Ig chain expression can be produced by injecting mice with antisera against one or more endogenous Ig chains (Weiss et al. (1984) Proc. Natl. Acad. Sci. (U.S.A.) 81 211, which is incorporated herein by reference). Antisera are selected so as to react specifically with one or more endogenous (e.g., murine) Ig chains but to have minimal or no cross-reactivity with heterologous Ig chains encoded by an Ig transgene of the invention. Thus, administration of selected antisera according to a schedule as typified by that of Weiss et al. will suppress endogenous Ig chain expression but permits expression of heterologous Ig chain(s) encoded by a transgene of the present invention. Suitable antibody sources for antibody comprise: (1) monoclonal antibodies, such as a monoclonal antibody that specifically binds to a murine $\mu$, $\gamma$, $\kappa$, or $\lambda$ chains but does not react with the human immunoglobulin chain(s) encoded by a human Ig transgene of the invention; (2) mixtures of such monoclonal antibodies, so that the mixture binds with multiple epitopes on a single species of endogenous Ig chain, with multiple endogenous Ig chains (e.g., murine $\mu$ and murine $\gamma$, or with multiple epitopes and multiple chains or endogenous immunoglobulins; (3) polyclonal antiserum or mixtures thereof, typically such antiserum/antisera is monospecific for binding to a single species of endogenous Ig chain (e.g., murine $\mu$, murine $\gamma$, murine $\kappa$, murine $\lambda$) or to multiple species of endogenous Ig chain, and most preferably such antisera possesses negligible binding to human immunoglobulin chains encoded by a transgene of the invention; and/or (4) a mixture of polyclonal antiserum and monoclonal antibodies binding to a single or multiple species of endogenous Ig chain, and most preferably possessing negligible binding to human immunoglobulin chains encoded by a transgene of the invention. Generally, polyclonal antibodies are preferred, and such substantially monospecific polyclonal antibodies can be advantageously produced from an antiserum raised against human immunoglobulin(s) by pre-adsorption with antibodies derived from the nonhuman animal species (e.g., murine) and/or, for example, by affinity chromatography of the antiserum or purified fraction thereof on an affinity resin containing immobilized human Ig (wherein the bound fraction is enriched for the desired anti-human Ig in the antiserum; the bound fraction is typically eluted with conditions of low pH or a chaotropic salt solution).

Cell separation and/or complement fixation can be employed to provide the enhancement of antibody-directed cell depletion of lymphocytes expressing endogenous (e.g., murine) immunoglobulin chains. In one embodiment, for example, antibodies are employed for ex vivo depletion of murine Ig-expressing explanted hematopoietic cells and/or B-lineage lymphocytes obtained from a transgenic mouse harboring a human Ig transgene. Thus, hematopoietic cells and/or B-lineage lymphocytes are explanted from a transgenic nonhuman animal harboring a human Ig transgene (preferably harboring both a human heavy chain transgene and a human light chain transgene) and the explanted cells are incubated with an antibody (or antibodies) which (1) binds to an endogenous immunoglobulin (e.g., murine $\mu$ and/or $\kappa$) and (2) lacks substantial binding to human immunoglobulin chains encoded by the transgene(s). Such antibodies are referred to as "suppression antibodies" for clarity. The explanted cell population is selectively depleted of cells which bind to the suppression antibody(ies); such depletion can be accomplished by various methods, such as (1) physical separation to remove suppression antibody-bound cells from unbound cells (e.g., the suppression antibodies may be bound to a solid support or magnetic bead to immobilize and remove cells binding to the suppression antibody), (2) antibody-dependent cell killing of cells bound by the suppression antibody (e.g., by ADCC, by complement fixation, or by a toxin linked to the suppression antibody), and (3) clonal energy induced by the suppression antibody, and the like.

Frequently, antibodies used for antibody suppression of endogenous Ig chain production will be capable of fixing complement. It is frequently preferable that such antibodies may be selected so as to react well with a convenient complement source for ex vivo/in vitro depletion, such as rabbit or guinea pig complement. For in vivo depletion, it is generally preferred that the suppressor antibodies possess effector functions in the nonhuman transgenic animal species; thus, a suppression antibody comprising murine effector functions (e.g., ADCC and complement fixation) generally would be preferred for use in transgenic mice.

In one variation, a suppression antibody that specifically binds to a predetermined endogenous immunoglobulin chain is used for ex vivo/in vitro depletion of lymphocytes expressing an endogenous immunoglobulin. A cellular explant (e.g., lymphocyte sample) from a transgenic nonhuman animal harboring a human immunoglobulin transgene is contacted with a suppression antibody and cells specifically binding to the suppression antibody are depleted (e.g., by immobilization, complement fixation, and the like), thus generating a cell subpopulation depleted in cells expressing endogenous (nonhuman) immunoglobulins (e.g., lymphocytes expressing murine Ig). The resultant depleted lymphocyte population (T cells, human Ig-positive B-cells, etc.) can be transferred into a immunocompatible (i.e., MHC-compatible) nonhuman animal of the same species and which is substantially incapable of producing endogenous antibody (e.g., SCID mice, RAG-1 or RAG-2 knockout mice). The reconstituted animal (mouse) can then be immunized with an antigen (or reimmunized with an antigen used to immunize the donor animal from which the explant was obtained) to obtain high-affinity (affinity matured) antibodies and B-cells producing such antibodies. Such B-cells may be used to generate hybridomas by conventional cell fusion and screened. Antibody suppression can be used in combination with other endogenous Ig inactivation/suppression methods (e.g., $J_H$ knockout, $C_H$ knockout, D-region ablation, antisense suppression, compensated frameshift inactivation).

Complete Endogenous Ig Locus Inactivation

In certain embodiments, it is desirable to effect complete inactivation of the endogenous Ig loci so that hybrid immunoglobulin chains comprising a human variable region and a non-human (e.g., murine) constant region cannot be formed (e.g., by trans-switching between the transgene and endogenous Ig sequences). Knockout mice bearing endogenous heavy chain alleles which are functionally disrupted in the $J_H$ region only frequently exhibit trans-switching, typically wherein a rearranged human variable region (VDJ) encoded by a transgene is expressed as a fusion protein linked to an endogenous murine constant region, although other trans-switched junctions are possible. To overcome this potential problem, it is generally desirable to completely inactivate the endogenous heavy chain locus by any of various methods, including but not limited to the following: (1) functionally disrupting and/or deleting by homologous recombination at least one and preferably all of the endogenous heavy chain constant region genes, (2) mutating at least one and preferably all of the endogenous heavy chain constant region genes to encode a termination codon (or frameshift) to produce a truncated or frameshifted product (if trans-switched), and other methods and strategies apparent to those of skill in the art. Deletion of a substantial portion or all of the heavy chain constant region genes and/or D-region genes may be accomplished by various methods, including sequential deletion by homologous recombination targeting vectors, especially of the "hit-and-run" type and the like. Similarly, functional disruption and/or deletion of at least one endogenous light chain locus (e.g., κ) to ablate endogenous light chain constant region genes is often preferable.

In a preferred embodiment the disruption is of both the endogenous mouse heavy- and κ-light chain immunoglobulin genes, as the antibodies that are generated and expressed in mice having such disruptions tend to originate from the introduced transgene(s). A preferred method for the disruption of the κ light chain locus is described in Chen et al. (1993) EMBO J. 12:811-820, which is hereby incorporated by reference in its entirety. Preferred methods for the homozygous disruption of the heavy chain locus include disruption of the mu heavy chain gene is described in Example 1 of PCT Publication WO 01/09187 (commonly referred to as the M or CMD disruption), and the J heavy chain gene disruption is described in U.S. Pat. No. 5,545,806 (commonly referred to as J or JHD disruption).

Frequently, it is desirable to employ a frameshifted transgene wherein the heterologous transgene comprises a frameshift in the J segment(s) and a compensating frameshift (i.e., to regenerate the original reading frame) in the initial region (i.e., amino-terminal coding portion) of one or more (preferably all) of the transgene constant region genes. Trans-switching to an endogenous IgH locus constant gene (which does not comprise a compensating frameshift) will result in a truncated or missense product that results in the trans-switched B cell being deleted or non-selected, thus suppressing the trans-switched phenotype.

Antisense suppression and antibody suppression may also be used to effect a substantially complete functional inactivation of endogenous Ig gene product expression (e.g., murine heavy and light chain sequences) and/or trans-switched antibodies (e.g., human variable/murine constant chimeric antibodies).

Various combinations of the inactivation and suppression strategies may be used to effect essentially total suppression of endogenous (e.g., murine) Ig chain expression.

Xenoenhancers

A heterologous transgene capable of encoding a human immunoglobulin (e.g., a heavy chain) advantageously comprises a cis-linked enhancer which is not derived from the mouse genome, and/or which is not naturally associated in cis with the exons of the heterologous transgene. For example, a human κ transgene (e.g., a κ minilocus) can advantageously comprise a human Vκ gene, a human Jκ gene, a human Cκ gene, and a xenoenhancer, typically said xenoenhancer comprises a human heavy chain intronic enhancer and/or a murine heavy chain intronic enhancer, typically located between a Jκ gene and the Cκ gene, or located downstream of the Cκ gene. For example, the mouse heavy chain J-µ intronic enhancer (Banerji et al. (1983) Cell 33: 729) can be isolated on a 0.9 kb XbaI fragment of the plasmid pKVe2 (see, infra). The human heavy chain J-µ intronic enhancer (Hayday et al. (1984) Nature 307: 334) can be isolated as a 1.4 kb MluI/HindIII fragment (see, infra). Addition of a transcriptionally active xenoenhancer to a transgene, such as a combined xenoenhancer consisting essentially of a human J-µ intronic enhancer linked in cis to a mouse J-µ intronic enhancer, can confer high levels of expression of the transgene, especially where said transgene encodes a light chain, such as human κ. Similarly, a rat 3' enhancer can be advantageously included in a minilocus construct capable of encoding a human heavy chain.

Specific Preferred Embodiments

Preferred embodiments of the instant invention include the use of one or more of the constructs identified in Table 1.

TABLE 1

| Construct Type | Example | Description |
| --- | --- | --- |
| Plasmid | pHC2 | ~80 kb minilocus transgene with 4 functional Vh segments, 15 D segments, 6 J segments, µ and γ1 coding exons (with switch regions), Jµ intronic enhancer, and rat 3' heavy chain enhancer. See Taylor, et al, Intl. Immunol. v.6 no. 4, pp579-591 (1994) |
| Plasmid | pGP69-7 VHC | ~28 kb transgene with 12 functional human Vh segments plus a 'homology cassette' at the 3' end to facilitate recombination with other constructs (e.g. VDJCE) |
| Plasmid | pVx6 | ~25 kb transgene with 3 functional Vh segments (5-51, 3-23, and 1-18; patent WO 01/09187) |
| BAC | VDJCE | ~240 kb engineered BAC which contains (in germline configuration) approximately 230 kb of the human heavy chain locus. 5' extent of sequence is approx 22 kb bp upstream of Vh 6-1, 3' extent is |

TABLE 1-continued

| Construct Type | Example | Description |
|---|---|---|
| | | approx 8.7 kb downstream of IgHγ1. Derived from BAC constructs CTD-2590A7 and -2194O15. A synthetic Ig enhancer derived from human Ig locus is appended to the 3' end. |
| BAC | V12DJCE | ~238 kb engineered BAC which contains the 12 Vh segments derived from pGP69-7 VHC integrated into the VDJCE BAC, approx ~8 kb upstream of the D region. |
| BAC | CTD-3054M17 | ~190 kb BAC clone containing human heavy chain Ig Vh segments (from Vh 4-39 at 5' end to Vh 3-23 at 3' end), in unrearranged germline configuration |
| BAC | BAC fusion #1 | ~196 kb BAC clone recombined from parental BAC CTD-2011A5 (Vh content spans 3-74 at 5' end to 3-53 at 3' end); "VHC" homology cassette appended to 3' end |
| BAC | BAC fusion #2 | ~217 kb BAC clone recombined from parental BACs CTD-3148C6 and CTD-3074B5 (Vh content spans from 3-53 at 5' end to 3-38 at 3' end); "VHC" homology cassette appended to 3' end |
| BAC | BAC fusion #3 | ~202 kb BAC clone recombined from parental BAC CTD-3054M17 (Vh content spans from 4-39 at 5' end to 3-23 at 3' end); "VHC" homology cassette appended to 3' end |
| BAC | BAC fusion #4 | ~227 kb BAC clone recombined from parental BACs CTD-2548B8 and CTD-2124N14 (Vh content spans from 3-23 at 5' end to 3-7 at 3' end); "VHC" homology cassette appended to 3' end |
| BAC | BAC fusion #5 | ~114 kb BAC clone derived from parental BAC CTD-2304I22 (Vh content spans from 3-7 at 5' end to 1-2 at 3' end); "VHC" homology cassette appended to 3' end |
| YAC | yIgH24a | ~460 kb YAC clone containing human heavy chain Ig Vh segments (from Vh 3-53 at 5' end to Vh 1-24 at 3' end), in unrearranged germline configuration. See patent application WO2005/058815 for description. |
| YAC | yIgH10 | ~375 kb YAC clone containing human heavy chain Ig Vh segments (from Vh 4-34 at 5' end to Vh 3-15 at 3' end), in unrearranged germline configuration |
| BAC-YAC | pIgYBac | ~500 kb bacterial-yeast shuttle vector containing all relevant Vh segments from yIgH10 plus entire VDJCE |

Specific examples of such embodiments including one or more of the above-described constructs include, but are not limited to, HCo20, HCo27, HCo28, HCo30, HCo31, HCo32, HCo33, and HCo34, each of which is described in detail in the Examples included below.

Figure 1A:
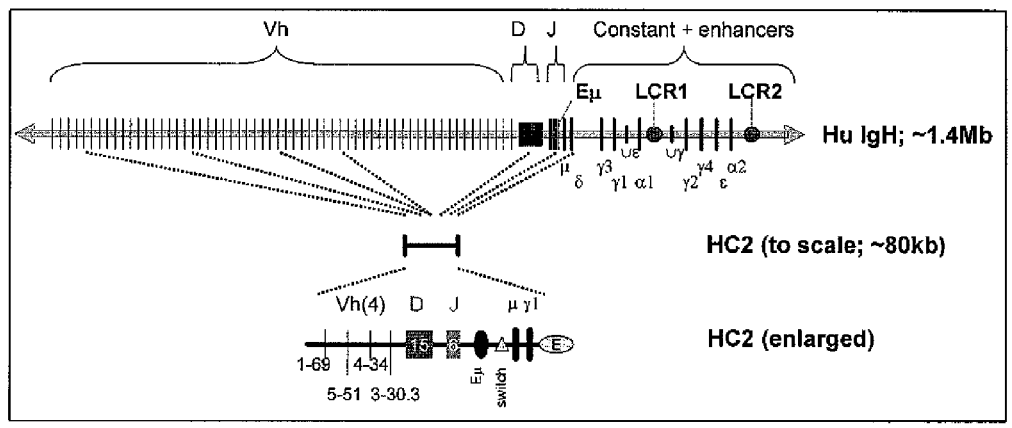
FIG. 1. Schematic depictions of minilocus transgenes. The native genomic human Ig heavy chain locus is depicted as a ~1.4 Mb region; it is divided into 4 functional subregions. The variable (Vh) region, diversity (D), joining (J), and constant region+enhancers are shown. In (A), the HC2 minigene is derived from discontinuous, joined fragments from all four functional sub-regions. As illustrated, it contains 4 Vh, 15 D, 6 J, 2 constant regions, as well as a rat 3' immunoglobulin enhancer. In (B), 12 selected Vh segments were derived from PCR amplification of genomic DNA templates, assembled head-to-tail in germline order, and appended with an immunoglobulin locus-derived fragment which is used to facilitate recombination between transgenes.
Figure 1B:
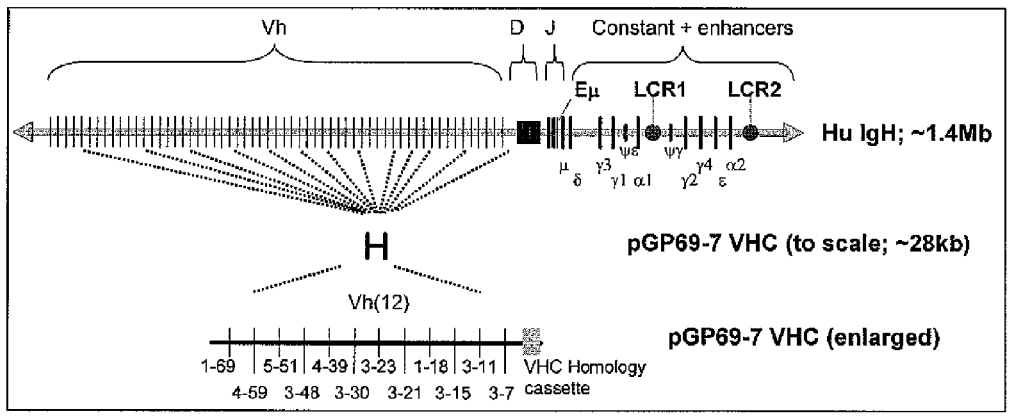
Figure 2:
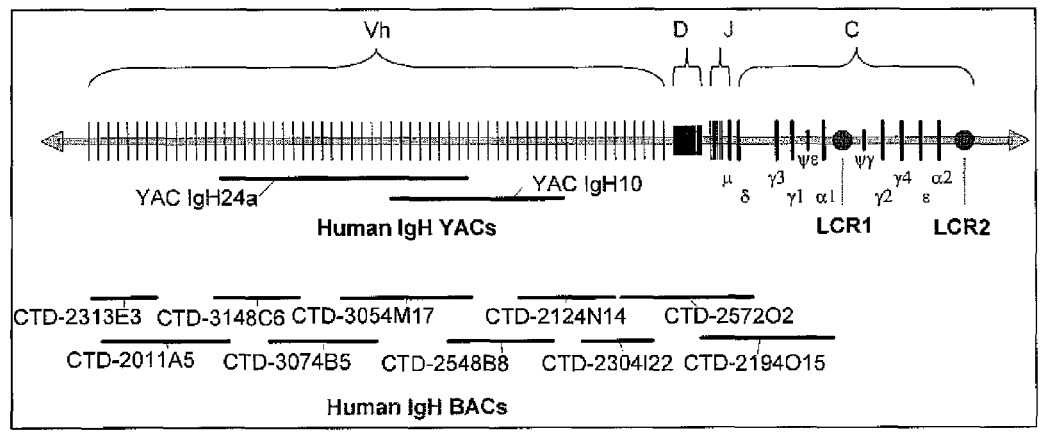
FIG. 2. Schematic of human Ig heavy chain genomic clones. As in FIG. 1, the human heavy chain Ig locus is depicted above, with functional regions indicated. YAC clones IgH24a and IgH10 are shown to scale, reflecting their relative position and boundaries within the Vh region.
Figure 3A:
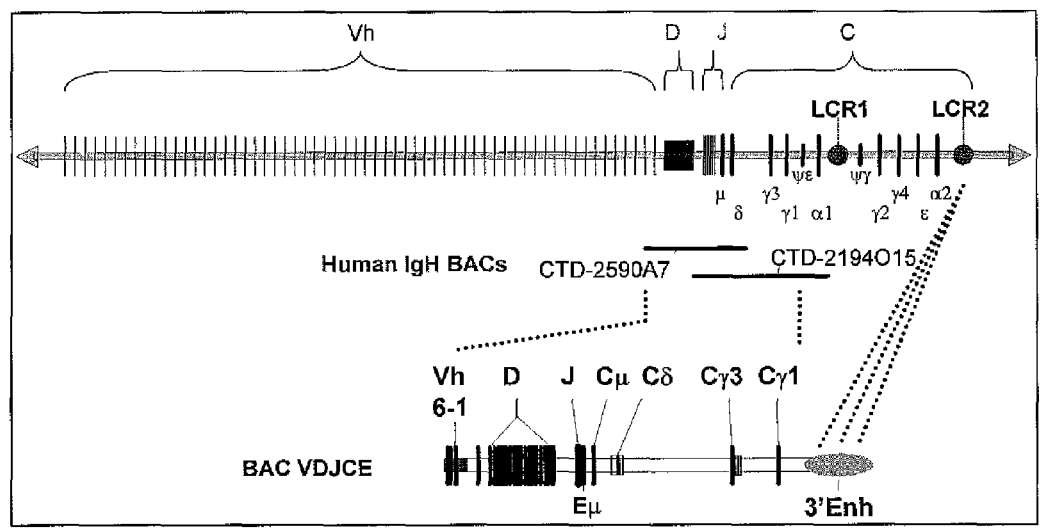
Figure 3B:
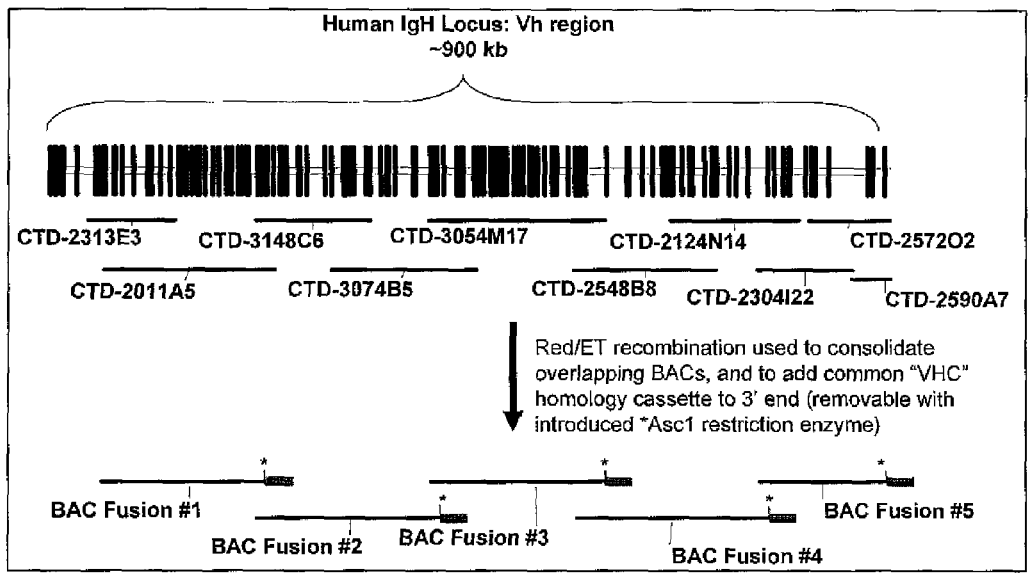
Figure 3C:
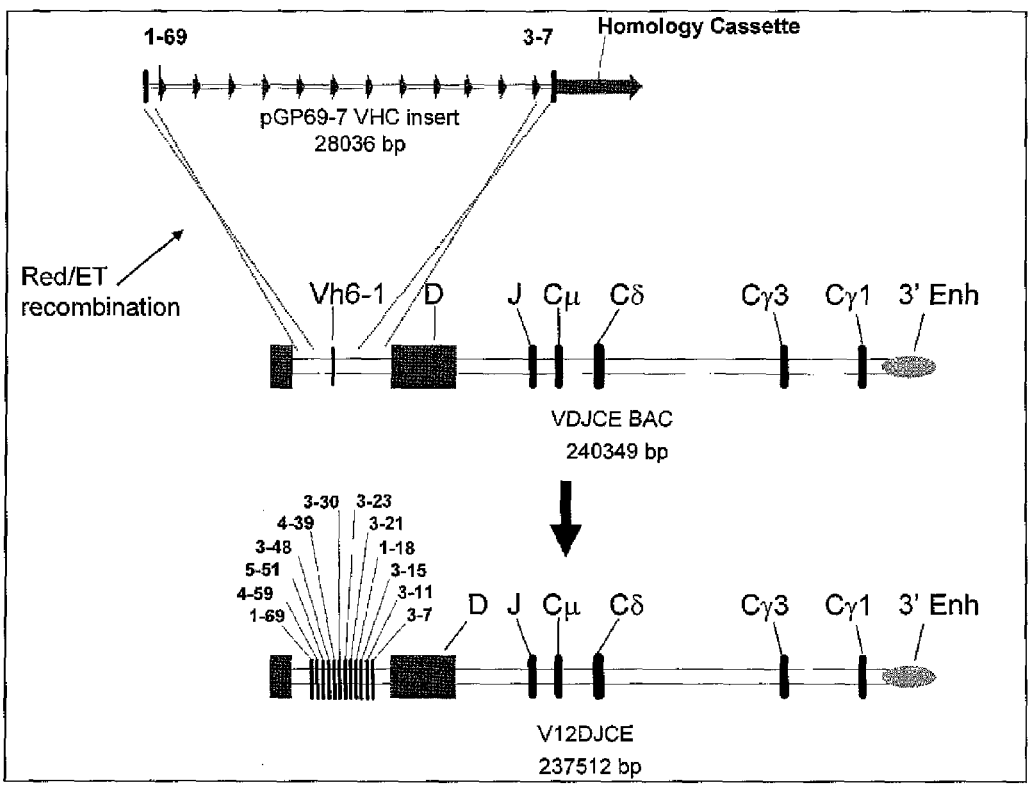
Figure 3D:
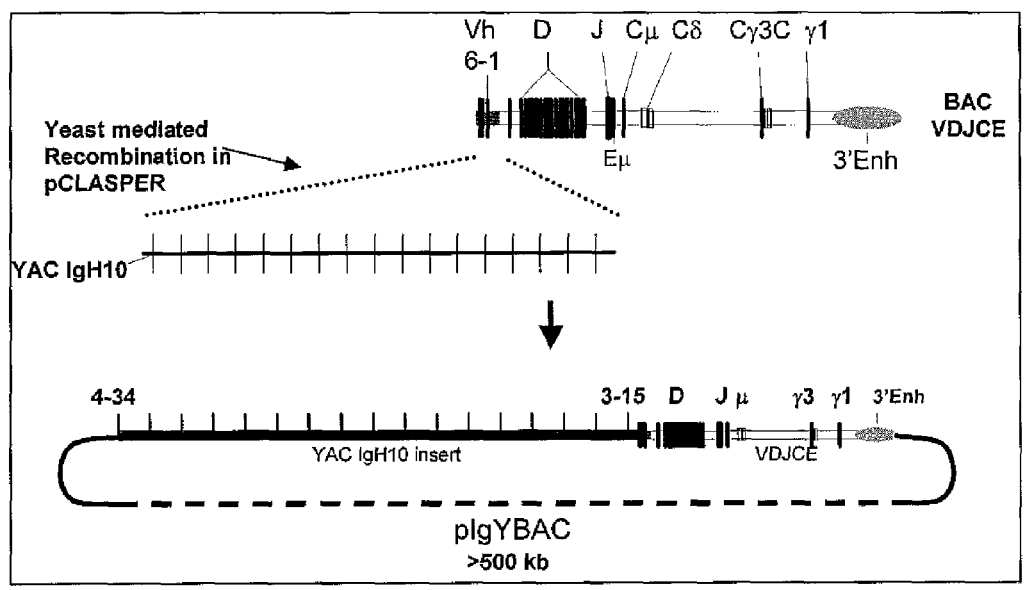

Additional embodiments include the use of the VDJCE BAC or V12DJCE inserts described in Table 1 co-injected with any single insert derived from the germline human IgH BAC clones depicted in FIG. 2. Further embodiments employ multiple germline human IgH BAC construct inserts co-injected with either the VDJCE or V12DJCE insert. Alternatively, the VDJCE BAC or V12DJCE insert can be co-injected with any single insert derived from the "BAC fusion" constructs (BAC fusion #1-5 identified in Table 1). In addition, as is the case for the IgH BAC constructs, multiple BAC fusion construct inserts can be co-injected with either of the VDJCE or V12DJCE inserts. Furthermore, the BAC fusion constructs can be isolated and injected with or without inclusion of the VHC homology cassette at the 3' end. In addition, either or both yIgH10 and yIgH24a inserts can be co-injected with either the VDJCE or V12DJCE insert. Similarly, pIgYBac can be co-injected with any combination of germline human IgH YAC clones, human IgH germline BAC clone inserts, or BAC fusion construct inserts described FIG. 2 and Table 1, again with or without the VHC cassettes at the 3' end of the BAC fusion constructs.

The BAC clones identified with the prefix "CTD-" listed in Table 1 and included in FIG. 2 are derived from the "CTD" human genome BAC library created by the Hiroaki Shizuya laboratory at the California Institute of Technology and which is commercially available from Open Biosystems. Detailed information relating to the coverage and construction of the BAC clones can be found at the California Institute of Technology's website: informa.bio.caltech.edu/idx_www_tree.html, the contents of which are hereby incorporated by reference in their entirety.

In some embodiments, it may be preferable to generate mice with predetermined repertoires to limit the selection of V genes represented in the antibody response to a predetermined antigen type. A heavy chain transgene having a predetermined repertoire may comprise, for example, human $V_H$ genes which are preferentially used in antibody responses to the predetermined antigen type in humans. Alternatively, some $V_H$ genes may be excluded from a defined repertoire for various reasons (e.g., have a low likelihood of encoding high affinity V regions for the predetermined antigen; have a low propensity to undergo somatic mutation and affinity sharpening; or are immunogenic to certain humans).

Thus, prior to rearrangement of a transgene containing various heavy or light chain gene segments, such gene segments may be readily identified, e.g. by hybridization or DNA sequencing, as being from a species of organism other than the transgenic animal.

The transgenic mice of the present invention can be immunized with a predetermined antigen, such as a transmembrane proteins, cell surface macromolecule, or other suitable antigen (e.g., TNF, LPS, etc.) for which a human antibody would be desirable. The mice will produce B cells which undergo class-switching via intratransgene switch recombination (cis-switching) and express immunoglobulins reactive with the predetermined antigen. The immunoglobulins can be human sequence antibodies, wherein the heavy and light chain polypeptides are encoded by human transgene sequences, which may include sequences derived by somatic mutation and V region recombinatorial joints, as well as germline-encoded sequences; these human sequence immunoglobulins can be referred to as being substantially identical to a polypeptide sequence encoded by a human $V_L$ or $V_H$ gene segment and a human $J_L$ or $J_L$ segment, even though other non-germline sequences may be present as a result of somatic mutation and differential V-J and V-D-J recombination joints. With respect to such human sequence antibodies, the variable regions of each chain are typically at least 80 percent encoded by human germline V, J, and, in the case of heavy chains, D, gene segments; frequently at least 85 percent of the variable regions are encoded by human germline sequences present on the transgene; often 90 or 95 percent or more of the variable region sequences are encoded by human germline sequences present on the transgene. However, since non-germline sequences are introduced by somatic mutation and VJ and VDJ joining, the human sequence antibodies will frequently have some variable region sequences (and less frequently constant region sequences) which are not encoded by human V, D, or J gene segments as found in the human transgene(s) in the germline of the mice. Typically, such non-germline sequences (or individual nucleotide positions) will cluster in or near CDRS, or in regions where somatic mutations are known to cluster.

The B cells from such mice can be used to generate hybridomas expressing monoclonal high affinity (greater than $2\times10^9$ $M^{-1}$) human sequence antibodies against a variety of antigens, including human proteins such as CD4 and the like. These hybridomas can be used to generate a composition comprising an immunoglobulin having an affinity constant ($K_a$) of at least $2\times10^9$ $M^{-1}$ for binding to a predetermined human antigen, wherein said immunoglobulin consists of: a human sequence light chain composed of (1) a light chain variable region having a polypeptide sequence which is substantially identical to a polypeptide sequence encoded by a human $V_L$ gene segment and a human $J_L$ segment, and (2) a light chain constant region having a polypeptide sequence which is substantially identical to a polypeptide sequence encoded by a human $C_L$ gene segment; and a human sequence heavy chain composed of a (1) a heavy chain variable region having a polypeptide sequence which is substantially identical to a polypeptide sequence encoded by a human $V_H$ gene segment, optionally a D region, and a human $J_H$ segment, and (2) a constant region having a polypeptide sequence which is substantially identical to a polypeptide sequence encoded by a human $C_H$ gene segment.

Often, the human sequence heavy chain and human sequence light chain are separately encoded by a human heavy chain transgene and a human light chain transgene, respectively, which are integrated into a mouse cell genome. However, both chains may be encoded on a single transgene, or one or both chains may be encoded on multiple transgenes.

In one embodiment, the invention provides a transgenic mouse comprising: a homozygous pair of functionally disrupted endogenous heavy chain alleles, a homozygous pair of functionally disrupted endogenous light chain alleles, at least one copy of a heterologous immunoglobulin light chain transgene, and at least one copy of a heterologous immunoglobulin heavy chain transgene, and wherein said animal makes an antibody response following immunization with a human antigen wherein the antibody response comprises an immunoglobulin having an affinity constant ($K_a$) of at least $2\times10^9$ $M^{-1}$ for binding to a predetermined human antigen, wherein said immunoglobulin consists of: a human sequence light chain composed of (1) a light chain variable region having a polypeptide sequence which is substantially identical to a polypeptide sequence encoded by a human $V_L$ gene segment and a human $J_L$ segment, and (2) a light chain constant region having a polypeptide sequence which is substantially identical to a polypeptide sequence encoded by a human $C_L$ gene segment; and a human sequence heavy chain composed of a (1) a heavy chain variable region having a polypeptide sequence which is substantially identical to a polypeptide sequence encoded by a human $V_H$ gene segment, optionally a D region, and a human $J_H$ segment, and (2) a constant region having a polypeptide sequence which is substantially identical to a polypeptide sequence encoded by a human $C_H$ gene segment.

In a preferred embodiment, the transgenes of the present invention are introduced into a HCo7/lambda mouse. In such HCo7/lambda mice, not only has the endogenous mouse kappa light chain gene has been homozygously disrupted as described in Chen et al. (1993) EMBO J. 12:811-820, but the endogenous mouse heavy chain gene has also been homozygously disrupted as described in Example 1 of PCT Publication WO 01/09187. Furthermore, such mice carry a human kappa light chain transgene, KCo5, as described in Fishwild et al. (1996) Nature Biotechnology 14:845-851, and a human heavy chain transgene, HCo7, as described in U.S. Pat. Nos. 5,545,806; 5,625,825; and 5,545,807. The mice also carry a human lambda light chain transgene composed of a yeast artificial chromosome containing most of the human Ig lambda locus, as described in PCT Publication WO 2000/26373. Through selective breeding, mice can be recovered which harbor homozygous gene disruptions of both heavy and light chains, contain the human heavy chain transgene, and in terms of light chain transgenes, contain either both κ and λ light chain transgenes, only the κ light chain transgene, or only the λ light chain transgene, All three genotypes can be used for immunizations and recovery of human antibodies.

In addition to employing mice having endogenous heavy and/or light chain locus disruptions, the development of high affinity human sequence antibodies against predetermined antigens is facilitated by a method for expanding the repertoire of human variable region gene segments in a transgenic mouse having a genome comprising an integrated human immunoglobulin transgene. One preferred method for accomplishing this comprises introducing into the genome a V gene transgene comprising V region gene segments which are not present in a previously integrated human immunoglobulin transgene. Often, the V region transgene comprises a portion of a human $V_H$ or $V_L$ (Vκ) gene segment array, as may naturally occur in a human genome or as may be spliced together separately by recombinant methods, which may include out-of-order or omitted V gene segments. Often at least five, 10, 20, or more functional V gene segments are introduced by this method. Examples of such transgenes include the inserts of pHC2, pGP69-7 VHC, pVx6, VDJCE, V12DJCE, CTD-3054M17, BAC fusion #1, BAC fusion #2, BAC fusion #3, BAC fusion #4, BAC fusion #5, yIgH24a, yIgH10, and pIgYBac, described above. In such a variation, it is possible to make a transgenic mouse produced by the V repertoire expansion method, wherein the mouse expresses an immunoglobulin chain comprising a variable region sequence encoded by a V region gene segment present on the V region transgene and a C region encoded on the human Ig transgene. By means of the V repertoire expansion method, transgenic mice having at least 5 distinct V genes can be generated; as can mice containing at least about 24 V genes or more. Of course, some V gene segments may be non-functional (e.g., pseudogenes and the like); these segments may be retained or may be selectively deleted by recombinant methods available to the skilled artisan, if desired.

Once the mouse germline has been engineered to contain an expanded V segment repertoire, the trait can be propagated and bred into other genetic backgrounds, including backgrounds where the expanded V segment repertoire is bred into a mouse germline having a different human Ig transgene. Multiple expanded V segment repertoires may be bred into a germline to work with a human Ig transgene (or multiple human Ig transgenes).

The invention also provides a method of propagating the trait of human sequence immunoglobulin expression, comprising breeding a transgenic mouse having the human Ig transgene(s), and optionally also having an expanded V segment repertoire. Both $V_H$ and $V_L$ gene segments may be present in the expanded V segment repertoire. The transgenic mouse may be bred into any background desired by the practitioner, including backgrounds harboring other human transgenes, including human Ig transgenes and/or transgenes encoding other human lymphocyte proteins. The transgenic mouse may furthermore be bred to mice harboring gene disruptions of other, non-immunoglobulin genes whose function may serve to alter antibody response or lymphocyte function.

In a preferred embodiment, such breeding involves breeding into the Balb/c strain described in detail in Example 12.

Pharmaceutical Compositions

In another aspect, the present invention provides a composition, e.g., a pharmaceutical composition, containing one or a combination of monoclonal antibodies, or antigen-binding portion(s) thereof, of the present invention, formulated together with a pharmaceutically acceptable carrier.

Pharmaceutical compositions of the invention also can be administered in combination therapy, i.e., combined with other agents. For example, the combination therapy can include an antibody of the present invention combined with at least one other anti-inflammatory or immunosuppressant agent. Examples of therapeutic agents that can be used in combination therapy are described in greater detail below in the section on uses of the antibodies of the invention.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the conjugated antibody and partner molecule may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 µg/ml and in some methods about 25-300 µg/ml.

Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an antibody of the invention preferably results in a decrease in severity of disease symptoms, an increase in frequency and duration of disease symptom-free periods, or a prevention of impairment or disability due to the disease affliction. For example, for the treatment of tumors, a "therapeutically effective dosage" preferably inhibits cell growth or tumor growth by at least about 20%, more preferably by at least about 40%, even more preferably by at least about 60%, and still more preferably by at least about 80% relative to untreated subjects. The ability of a compound to inhibit tumor growth can be evaluated in an animal model system predictive of efficacy in human tumors. Alternatively, this property of a composition can be evaluated by examining the ability of the compound to inhibit cell growth, such inhibition can be measured in vitro by assays known to the skilled practitioner. A therapeutically effective amount of a therapeutic compound can decrease tumor size, or otherwise ameliorate symptoms in a subject. One of ordinary skill in the art would be able to determine such amounts based on such factors as the subject's size, the severity of the subject's symptoms, and the particular composition or route of administration selected.

A composition of the present invention can be administered via one or more routes of administration using one or more of a variety of methods known in the art. As will be appreciated by the skilled artisan, the route and/or mode of administration will vary depending upon the desired results. Preferred routes of administration for antibodies of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody of the invention can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Therapeutic compositions can be administered with medical devices known in the art. For example, in a preferred embodiment, a therapeutic composition of the invention can be administered with a needleless hypodermic injection device, such as the devices disclosed in U.S. Pat. No. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable microinfusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the human monoclonal antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) J. Clin. Pharmacol. 29:685). Exemplary targeting moieties include folate or biotin (see, e.g., U.S. Pat. No. 5,416,016 to Low et al.); mannosides (Umezawa et al., (1988) Biochem. Biophys. Res. Commun. 153:1038); antibodies (P. G. Bloeman et al. (1995) FEBS Lett. 357:140; M. Owais et al. (1995) Antimicrob. Agents Chemother. 39:180); surfactant protein A receptor (Briscoe et al. (1995) Am. J. Physiol. 1233:134); p120 (Schreier et al. (1994) J. Biol. Chem. 269:9090); see also K. Keinanen; M. L. Laukkanen (1994) FEBS Lett. 346:123; J. J. Killion; I. J. Fidler (1994) Immunomethods 4:273.

The human-sequence monoclonal antibodies of the invention are useful, in part, because they bind specifically to the predetermined antigen against which they are directed. When the predetermined antigen is a human antigen (i.e., a human protein or fragment thereof), it will sometimes be advantageous if the human immunoglobulin of the invention also binds to the cognate antigen found in non-human animals, especially animals that are used frequently for drug testing (e.g., preclinical testing of biological activity, pharmacokinetics and safety). These animals include mice, rabbits, rats, dogs, pigs, and, especially, non-human primates such as chimpanzees, apes and monkeys (e.g., Rhesus monkeys and cynomolgus monkeys). The ability to recognize antigens in experimental animals is particularly useful for determining the effect of specific binding on biodistribution of the immunoglobulins. A cognate antigen is an antigen that (i) has a structure (e.g., amino acid sequence) that is substantially similar to the human antigen (i.e., the amino acid sequence of an animal cognate protein will typically be at least about 50% identical to the human protein, usually at least about 70% identical and often at least about 80% identical or more); (ii) has substantially the same function as the human antigen; and, (iii) often is found in the same cellular compartment as the human antigen. Human and animal cognate antigens typically (but not always) have the same names. Examples of cognate antigens include human tubulin and mouse tubulin, human CD4 and Rhesus CD4, and human IgG and Rat IgG.

Selection and Engineering of Antibodies

The instant invention provides a method for identifying candidate hybridomas which secrete a monoclonal antibody comprising a human immunoglobulin chain consisting essentially of a human VDJ sequence in polypeptide linkage to a human constant region sequence. Such candidate hybridomas are identified from a pool of hybridoma clones comprising: (1) hybridoma clones that express immunoglobulin chains consisting essentially of a human VDJ region and a human constant region, and (2) trans-switched hybridomas that express heterohybrid immunoglobulin chains consisting essentially of a human VDJ region and a murine constant region. The supernatant(s) of individual or pooled hybridoma clones is contacted with a predetermined antigen, typically an antigen which is immobilized by adsorption onto a solid substrate (e.g., a microtitre well), under binding conditions to select antibodies having the predetermined antigen binding specificity. An antibody that specifically binds to human constant regions is also contacted with the hybridoma supernatant and predetermined antigen under binding conditions so that the antibody selectively binds to at least one human constant region epitope but substantially does not bind to murine constant region epitopes; thus forming complexes consisting essentially of hybridoma supernatant (transgenic monoclonal antibody) bound to a predetermined antigen and to an antibody that specifically binds human constant regions (and which may be labeled with a detectable label or reporter). Detection of the formation of such complexes indicates hybridoma clones or pools which express a human immunoglobulin chain.

In a preferred embodiment of the invention, the anti-human constant region immunoglobulin used in screening specifically recognizes a non-µ, non-δ isotype, preferably a α or ε, more preferably a γ isotype constant region. Monoclonal antibodies of the γ isotype are preferred (i) because the characteristics of IgG immunoglobulins are preferable to IgM immunogloblins for some therapeutic applications (e.g., due to the smaller size of the IgG dimers compared to IgM pentamers) and, (ii) because the process of somatic mutation is correlated with the class switch from the µ constant region to the non-µ (e.g., γ) constant regions. Immunoglobulins selected from the population of immunoglobulins that have undergone class switch (e.g., IgG) tend to bind antigen with higher affinity than immunoglobulins selected from the population that has not undergone class switch (e.g., IgM). See, e.g., Lonberg and Huszar. Intern. Rev. Immunol. 13:65-93 (1995) which is incorporated herein by reference.

In one embodiment the candidate hybridomas are first screened for the γ isotype constant region and the pool of IgG-expressing hybridomas is then screened for specific binding to the predetermined antigen.

Thus, according to the method, a transgenic mouse of the invention is immunized with the predetermined antigen to induce an immune response. B cells are collected from the mouse and fused to immortal cells to produce hybridomas. The hybridomas are first screened to identify individual hybridomas secreting Ig of a non-µ, non-δ isotype (e.g., IgG). This set of hybridomas is then screened for specific binding to the predetermined antigen of interest. Screening is carried out using standard techniques as described in, e.g., Harlow and Lane, Antibodies: A Laboratory Manual, Cold Spring Harbor, N.Y. (1988). Using this method it is possible to identify high-affinity immunoglobulins (e.g., $K_a$ greater than about $10^7$ $M^{-1}$) practically and efficiently.

An other aspect, the invention provides antigen-binding human monoclonal antibodies comprising at least one polypeptide encoded by an artificial gene. An artificial gene comprises a polypeptide-encoding nucleic acid segment that is synthesized in vitro by chemical or enzymatic methods that do not require a cell-derived template nucleic acid strand (e.g., a nucleic acid template obtained from a bacterial cell or an immune or hybridoma cell) and the progeny (through replication) of the artificial gene, i.e., a wholly synthetic nucleic acid.

Although it is routine in genetic engineering to use short synthetic nucleic acids as primers, linkers and the like, it is also possible by chemical and/or enzymatic means to produce wholly synthetic protein-coding nucleic acids that are 30, 50, or more bases in length. The artificial genes of the invention may include both synthetic nucleic acid regions and cell-derived nucleic acid regions. The synthetic nucleic acid region of the artificial gene will generally be at least about 50 bases in length, often at least about 100 bases, typically at least about 200 bases, more often at least about 250 bases and usually over 300 bases or 400 bases in length. Typically the synthetic nucleic acid regions will encode variable gene segments or a portion thereof, e.g., CDR regions, and the constant regions will be encoded by cell-derived nucleic acids. Immunoglobulin polypeptides (i.e., immunoglobulin heavy chains and immunoglobulin light chains) can be conveniently expressed using artificial genes that encode the polypeptides. Usually the artificial genes are operably linked to transcription promoter sequences, e.g., promoter sequences derived from immunoglobulin genes or from viruses (e.g., SV40, CMV, HIV, RSV) or hybrid promoters. The artificial gene may be linked to other sequences as well, e.g. polyadenylation sequences and introns. One method for expressing an immunoglobulin polypeptide involves insertion of a synthetic nucleic acid encoding one region of an immunoglobulin polypeptide (e.g., a variable region or portion thereof) into a vector that encodes the remaining segments or parts of the immunoglobulin chain (e.g., aµ, γ, γ2, γ3, γ4, δ, ε, $\alpha.sub.1$ or $\alpha.sub.2$ constant region) and, optionally, promoter (e.g., a CMV (cytomegalovirus) promoter), polyadenylation or other sequences. Such vectors are constructed so that upon introduction into a cell, the cellular transcription and translation of the vector sequences results in an immunoglobin polypeptide.

Functional human sequence immunoglobulin heavy and light chain genes and polypeptides can be constructed using artificial genes, and used to produce immunoglobulins with a desired specificity such as specific binding to a predetermined antigen. This is accomplished by constructing an artificial gene that encodes an immunoglobulin polypeptide substantially similar to a polypeptide expressed by a cell from, or a hybridoma derived from, a transgenic animal immunized with the predetermined antigen. Thus, the invention provides artificial genes encoding immunoglobulin polypeptides and methods for producing a human-sequence immunoglobulin using an artificial gene(s).

According to this method, a transgenic animal (e.g., a transgenic mouse with a homozygous pair of functionally disrupted endogenous heavy chain alleles, a homozygous pair of functionally disrupted endogenous light chain alleles, at least one copy of a human immunoglobulin light chain transgene, and at least one copy of a human immunoglobulin heavy chain transgene) is immunized with predetermined antigen, e.g., a human protein. Nucleic acid, preferably mRNA, is then collected or isolated from a cell or population of cells in which immunoglobulin gene rearrangement has taken place, and the sequence(s) of nucleic acids encoding the heavy and/or light chains (especially the V segments) of immunoglobulins, or a portion thereof, is determined. This sequence information is used as a basis for the sequence of the artificial gene.

Sequence determination will generally require isolation of at least a portion of the gene or cDNA of interest, e.g., a portion of a rearranged human transgene or corresponding cDNA encoding an immunoglobulin polypeptide. Usually this requires cloning the DNA or, preferably, mRNA (i.e., cDNA) encoding the human immunoglobulin polypeptide. Cloning is carried out using standard techniques (see, e.g., Sambrook et al. (2001) Molecular Cloning: A Laboratory Guide, Vols 1-3, 3rd edition, Cold Spring Harbor Press, which is incorporated herein by reference). For example, a cDNA library may be constructed by reverse transcription of polyA+ mRNA, preferably membrane-associated mRNA, and the library screened using probes specific for human immunoglobulin polypeptide gene sequences. In a preferred embodiment, however, the polymerase chain reaction (PCR) is used to amplify cDNAs (or portions of full-length cDNAs) encoding an immunoglobulin gene segment of interest (e.g., a light chain variable segment). Because the sequences of the human immunoglobulin polypeptide genes are readily available to those of skill, probes or PCR primers that will specifically hybridize to or amplify a human immunoglobulin gene or segment thereof can be easily designed. See, e.g., Taylor et al., Nuc. Acids. Res., 20:6287 (1992) which is incorporated by reference. Moreover, the sequences of the human transgene of the transgenic mouse will often be known to the practitioner, and primer sequences can be chosen that hybridize to appropriate regions of the transgene. The amplified sequences can be readily cloned into any suitable vector, e.g., expression vectors, minigene vectors, or phage display vectors. It will be appreciated that the particular method of cloning used not critical, so long as it is possible to determine the sequence of some portion of the immunoglobulin polypeptide of interest. As used herein, a nucleic acid that is cloned, amplified, tagged, or otherwise distinguished from background nucleic acids such that the sequence of the nucleic acid of interest can be determined, is considered isolated.

One source for RNA used for cloning and sequencing is a hybridoma produced by obtaining a B cell from the transgenic mouse and fusing the B cell to an immortal cell. An advantage of using hybridomas is that they can be easily screened, and a hybridoma that produces a human monoclonal antibody of interest selected. Alternatively, RNA can be isolated from B cells (or whole spleen) of the immunized animal. When sources other than hybridomas are used, it may be desirable to screen for sequences encoding immunoglobulins or immunoglobulin polypeptides with specific binding characteristics. One method for such screening is the use of phage display technology. Phage display is described in e.g., Phage Display: A Practical Approach, Clackson and Lowman Eds., Oxford University Press, USA (2004); Dower et al., WO 91/17271, McCafferty et al., WO 92/01047, and Caton and Koprowski, Proc. Natl. Acad. Sci. USA, 87:6450-6454 (1990), each of which is incorporated herein by reference. In one embodiment using phage display technology, cDNA from an immunized transgenic mouse (e.g., total spleen cDNA) is isolated, the polymerase chain reaction is used to amplify a cDNA sequences that encode a portion of an immunoglobulin polypeptide, e.g., CDR regions, and the amplified sequences are inserted into a phage vector. cDNAs encoding peptides of interest, e.g., variable region peptides with desired binding characteristics, are identified by standard techniques such as panning.

The sequence of the amplified or cloned nucleic acid is then determined. Typically the sequence encoding an entire variable region of the immunoglobulin polypeptide is determined, however, it will sometimes by adequate to sequence only a portion of a variable region, for example, the CDR-encoding portion. Typically the portion sequenced will be at least 30 bases in length, more often based coding for at least about one-third or at least about one-half of the length of the variable region will be sequenced.

Sequencing can be carried on clones isolated from a cDNA library, or, when PCR is used, after subcloning the amplified sequence or by direct PCR sequencing of the amplified segment. Sequencing is carried out using standard techniques (see, e.g., Sambrook et al. (2001) Molecular Cloning: A Laboratory Guide, Vols 1-3, 3rd edition, Cold Spring Harbor Press, and Sanger, F. et al. (1977) Proc. Natl. Acad. Sci. USA 74: 5463-5467, which is incorporated herein by reference). By comparing the sequence of the cloned nucleic acid with published sequences of human immunoglobulin genes and cDNAs, one of skill will readily be able to determine, depending on the region sequenced, (i) the germline segment usage of the hybridoma immunoglobulin polypeptide (including the isotype of the heavy chain) and (ii) the sequence of the heavy and light chain variable regions, including sequences resulting from N-region addition and the process of somatic mutation. One source of immunoglobulin gene sequence information is the National Center for Biotechnology Information, National Library of Medicine, National Institutes of Health, Bethesda, Md.

In an alternative embodiment, the amino acid sequence of an immunoglobulin of interest may be determined by direct protein sequencing.

An artificial gene can be constructed that has a sequence identical to or substantially similar to, at least a portion of the immunoglobulin-expressing gene (i.e., rearranged transgene). Similarly, the artificial gene can encode an polypeptide that is identical or has substantial similarity to a polypeptide encoded by the sequenced portion of the rearranged transgene. The degeneracy of the genetic code allows the same polypeptide to be encoded by multiple nucleic acid sequences. It is sometimes desirable to change the nucleic acid sequence, for example to introduce restriction sites, change codon usage to reflect a particular expression system, or to remove a glycosylation site. In addition, changes in the hybridoma sequences may be introduced to change the characteristics (e.g., binding characteristics) of the immunoglobulin. For example, changes may be introduced, especially in the CDR regions of the heavy and light chain variable regions, to increase the affinity of the immunoglobulin for the predetermined antigen.

Methods for constructing an synthetic nucleic acids are well known. An entirely chemical synthesis is possible but in general, a mixed chemical-enzymatic synthesis is carried out in which chemically synthesized oligonucleotides are used in ligation reactions and/or in the polymerase chain reaction to create longer polynucleotides. In a preferred embodiment, the polymerase chain reaction is carried out using overlapping primers chosen so that the result of the amplification is a DNA with the sequence desired for the artificial gene. The oligonucleotides of the present invention may be synthesized in solid phase or in solution. Generally, solid phase synthesis is preferred. Detailed descriptions of the procedures for solid phase synthesis of oligonucleotides by phosphite-triester, phosphotriester, and H-phosphonate chemistries are widely available. See, for example, Itakura, U.S. Pat. No. 4,401,796; Caruthers et al., U.S. Pat. Nos. 4,458,066 and 4,500,707; Beaucage et al., Tetrahedron Lett., 22:1859-1862; Matteucci et al., J. Amer. Chem. Soc., 103: 3185-3191 (1981); Caruthers et al., Genetic Engineering, 4:1-17 (1982); Jones, chapter 2, Atkinson et al., chapter 3, and Sproat et al., chapter 4, in Gait, ed. Oligonucleotide Synthesis: A Practical Approach, IRL Press, Washington, D.C. (1984); Froehler et al., Tetrahedron Lett., 27:469-472 (1986); Froehler et al., Nucleic Acids Res., 14:5399-5407 (1986); Sinha et al., Tetrahedron Lett., 24:5843-5846 (1983); and Sinha et al., Nucleic Acids Res., 12:4539-4557 (1984) which are incorporated herein by reference.

The artificial gene can introduced into a cell and expressed to produce an immunoglobulin polypeptide. The choice of cell type for expression will depend on many factors (e.g., the level of protein glycosylation desired), but cells capable of secreting human immunoglobulins will be preferred. Especially preferred cells include CHO cells and myeloma-derived cells such as the SP20 and NS0 cell lines. Preferred mammalian host cells for expressing the recombinant antibodies of the invention include Chinese Hamster Ovary (CHO cells) (including dhfr− CHO cells, described in Urlaub and Chasin, (1980) Proc. Natl. Acad. Sci. USA 77:4216-4220, used with a DHFR selectable marker, e.g., as described in R. J. Kaufman and P. A. Sharp (1982) J. Mol. Biol. 159:601-621), NSO myeloma cells, COS cells and SP2 cells. In particular, for use with NSO myeloma cells, another preferred expression system is the GS gene expression system disclosed in WO 87/04462 (to Wilson), WO 89/01036 (to Bebbington) and EP 338,841 (to Bebbington). When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods. Methods for introduction of nucleic acids, e.g., an artificial gene, are well known and include transfection (e.g., by electroporation or liposome-mediated) and transformation. Systems for expression of introduced genes are described generally in Sambrook et al., supra.

In another embodiment, the antibody is produced as a UniBody as described in WO/2007/059782 which is incorporated herein by reference in its entirety.

It is often desirable to express two immunoglobulin polypeptides (i.e., a heavy chain and a light chain) in the same cell so that an immunoglobulin (e.g., an IgG molecule) is produced in vivo. Accordingly it will sometimes be desirable to introduce two artificial genes (i.e., one encoding a heavy chain and one encoding a light chain) into a cell. (The two artificial genes can be introduced on a single vector). Alternatively, one artificial gene encoding one immunoglobulin polypeptide can be introduced into a cell that has been genetically engineered to express the other immunoglobulin polypeptide.

It will be apparent that as the cells into which the artificial gene is transfected propagate, the wholly synthetic nucleic acid portion of the artificial gene, will act as a template for replication and transcription. Nonetheless, the progeny genes will have originated from a synthetic nucleic acid (i.e., a polypeptide-encoding nucleic acid molecule that is synthesized in vitro by chemical or enzymatic methods that do not require a cell-derived template nucleic acid strand) and as used herein, are also considered artificial genes. Thus, the relationship of the synthetic portion of the artificial gene to the expressed transgene of the hybridoma is one in which there is an informational link (i.e., sequence information) but no direct physical link.

EXAMPLES

Example 1. Preparation of pGP69-7 VHC

In order to construct pGP69-7 VHC germline $V_h$ regions were first amplified by polymerase chain reaction (PCR), using specific human IgH BAC constructs as template material for amplification; oligonucleotide primers specific to each individual $V_h$ region were designed, and the reactions were carried out using InVitrogen's Accuprime Pfx polymerase Supermix. The table below lists the specific oligonucleotides, and the cognate BAC templates used. Primer pairs were designed such that the coding regions of each $V_h$ segment were flanked by 700-1000 bp of both 5' and 3' genomic sequence (relative to initiator methionine and stop codon, respectively), ensuring that relevant promoters, octamer enhancers, and heptamer and nonamer recombination signals were present in each amplicon. In the table below, underlined nucleotides are specific to the $V_h$-region of interest; non-underlined lettering corresponds to added nucleotides for overlap PCR or the addition of specific restriction sites. Sense oligonucleotides are listed in the table first, which are then followed by antisense.

| Vh Region | BAC Template | Oligo Sequence (5'-3') |
|---|---|---|
| 1-69 | CTD-2011A5 | GTCGACTTGGTAATTATTTTGGGAGC;<br>AACAGGTCAGGTAAACCAGAAGTAAGATAAGC<br>(SEQ ID NO: 9) |
| 4-59 | CTD-2011A5 | TCTGGTTTACCTGACCTGTTATAGAGTTTTTG<br>AGCACCTTCTACAGGAGTGGGTGGCTTAAAC<br>(SEQ ID NO: 10); |
| 5-51 | CTD-3148C6 | CCACTCCTGTAGAAGGTGCTGGGGTTGACAC<br>(SEQ ID NO: 12);<br>GATGATAAACTTTCTCCACGTTTGCCAGACC<br>(SEQ ID NO: 13) |
| 3-48 | CTD-3148C6 | CGTGGAGAAAGTTTATCATCTTTCAATTAAGCCTC<br>(SEQ ID NO: 14);<br>CTCGAGATTTTCCAGGCAATAGTGAGTG<br>(SEQ ID NO: 15) |
| 4-39 | CTD-3054M17 | GTCGACGAGTTTTTGTCTGAAGTTCTCAC<br>(SEQ ID NO: 16);<br>AATGTAGACCGTCTGAATGTAGAAGATCAAGG<br>(SEQ ID NO: 17) |
| 3-30 | CTD-3054M17 | ACATTCAGACGGTCTACATTTTTCAAATCATTCACC<br>(SEQ ID NO: 18);<br>TCATGTTGGTGGTGATTAAGCAGCTTCAGC<br>(SEQ ID NO: 19) |
| 3-23 | CTD-3054M17 | CTTAATCACCACCAACATGAGAAATGTATGACAC<br>(SEQ ID NO: 20);<br>TTTCCATTTGGAAAATGGGGAGAGAAGG<br>(SEQ ID NO: 21) |

-continued

| Vh Region | BAC Template | Oligo Sequence (5'-3') |
|---|---|---|
| 3-21 | CTD-2548B8 | CCCCATTTTC<u>CAAATGGAAATTTAGACAAGCACGG</u> (SEQ ID NO: 22); CTCGAG<u>ACGACAACAGGAGAGTCC</u> (SEQ ID NO: 23) |
| 1-18 | CTD-2548B8 | GTCGAC<u>TCTGTGAGATCAGACAGGAACC</u> (SEQ ID NO: 24); GGTTCACGAGGGAGAGTCTATTCATATGGG (SEQ ID NO: 25) |
| 3-15 | CTD-2548B8 | AGACTCTCCC<u>TCGTGAACCCTAGTTCTCACC</u> (SEQ ID NO: 26); TTCCTCAGCC<u>TCCAAACCTCAGCATCACTCAG</u> (SEQ ID NO: 27) |
| 3-11 | CTD-2124N14 | GAGGTTTGGA<u>GGCTGAGGAAGAGCAAGAAAGAG</u> (SEQ ID NO: 28); CTTCAAAAT<u>GTGCACAGAAGACAAGAGTGTCC</u> (SEQ ID NO: 29) |
| 3-7 | CTD-2124N14 | CTTCTGTGCA<u>CATTTTGAAGCTGAGTTGCAGG</u> (SEQ ID NO: 30); CTCGAG<u>AAGACAACAGGAGTGTCCAG</u> (SEQ ID NO: 31) |

Using standard molecular biological methods, product amplicons were joined in a head-to-tail fashion and in germline orientation, and incorporated into the plasmid vector pGP2-1 together with a 4.9 kb fragment called the "VHC homology cassette". The VHC homology cassette is derived from the 5' end of human IgH BAC clone CTD-2590A7, and appended to the 3' end of the V.sub.h minigene cluster. This 4.9 kb fragment was PCR-amplified from BAC CTD-2590A7 using the following sense and antisense primers, respectively: 5'GCGGCCGC CTGTTTACTCTGATG-GTAGTT3' (SEQ ID NO:32), 5'GGCGCGCCGTTC-CTAGCCAAGGGAAGCGG3' (SEQ ID NO:33) (underlined sequence is specific to BAC CTD-2590A7, while the 8 nt at the 5' ends encode NotI and AscI restriction sites respectively). The VHC homology cassette is identical in sequence to the 5' end of BAC CTD-2590A7 and BAC VDJCE; thus, when pGP69-7 VHC is co-injected with either of these constructs, the overlap will favor homologous recombination and co-integration in a head-to-tail fashion. The final pGP69-7 VHC construct is 31 kb in size; vector (3 kb) and insert (28 kb) can be released from each other by SalI/NotI double digestion.

Example 2: Construction of BAC VDJCE

BAC VDJCE is composed of three primary elements. The first is a synthetic, tripartite human immunoglobulin enhancer derived from the region downstream of IgHα2, while the second and third elements are derived from human IgH BAC clones CTD-2194O15 and CTD-2590A7, respectively. BAC VDJCE was constructed using standard molecular biology techniques such as red/ET recombineering technology (described in Nat. Biotechnol. Vol 21, pp 443-447, (2003), which is hereby incorporated by reference in its entirety).

The tripartite human enhancer was designed based on enhancer analysis carried out by Hu, et al (3. Immunol, vol. 164, pp 6380-86, (2000)). The three separate enhancer elements Hs3, Hs1, 2, and Hs4 were amplified using the following three primer pairs, respectively (all in 5' to 3' orientation): ACGC<u>GTTCCTGACCGCTGAGCCCT</u> (SEQ ID NO:34) and <u>GTCGACCTGGAAAGCCCTAGCTGA</u> (SEQ ID NO:35), CTCG<u>AGCGTTGGCTCCCCTGCCCT</u> (SEQ ID NO:36) and GAT<u>ATCCTGGCCTTTTGCCAGTCCTC</u> (SEQ ID NO:37), CCC<u>GGGACGCTCGCTGCCCCACTC</u> (SEQ ID NO:38), and GGCGC<u>GCCTGGGACCTCCATGCAGG</u> (SEQ ID NO:39). Underlined sequence corresponds to gene-specific regions, while non-underlined sequence was added to create restriction enzyme cloning sites. The three amplicons of ~720, ~1107, and ~491 bp were generated by PCR amplification using either human genomic DNA or BAC RP11-731F5 as template material. These were all separately cloned into the pCR2.1 TOPO vector (InVitrogen). Using the unique restriction enzyme sites created by the primer 5' end sequences, a single, consolidated plasmid construct was generated which contained Hs3, Hs1,2, and Hs4 in a tandem, germline orientation (called pCRHs3/1,2/4).

The first step of recombineering for VDJCE BAC involved red/ET-based recombination and insertion of an expression cassette encoding zeocin resistance downstream of the Hs4 enhancer in pCRHs3/1,2/4, creating plasmid pCRHs3/1,2/4zeo. PCR amplification of the fragment containing the enhancers plus zeocin resistance gene from pCRHs3/1,2/4zeo were carried out using gene-specific primers flanked by primer sequences homologous to the 3' end of BAC CTD-2194O15. Insertion of the enhancer-zeocin cassette under zeocin selection resulted in incorporation of this fragment into BAC CTD-2194O15, in a region approximately 8.5 kb downstream of the termination codon for human IgHγ1. As a result, approximately 28 kb of human sequence which was originally in CTD-2194O15 downstream of the insertion site for the enhancer-zeocin cassette was deleted. This construct is hereafter referred to as "downstream BAC".

BAC CTD-2590A7 was also modified by red/ET recombineering, to incorporate a kanamycin resistance cassette within the vector backbone. This recombineered BAC was then referred to as "upstream BAC".

Downstream BAC was digested with PmeI+NruI restriction enzymes, and the 85 kb released fragment was isolated and purified; this fragment spanned a region from ~24 kb downstream of the IgHδ constant region domain through the zeocin resistance gene cassette. At its 5' end, it contained a ~4 kb overlap to the 3' end of the insert contained in upstream BAC; at its 3' end it contained ~1.3 kb overlap to the BAC vector sequence. Red/ET-based recombination between the downstream BAC fragment and upstream BAC were then carried out, and double selection with kanamycin and zeocin was performed, to ensure that both components were present in the final construct. The final product of this recombineering, VDJCE, was verified by PCR amplification of relevant junctions, and direct sequencing of selected junctions. In summary, the BAC VDJCE construct contains the following sequences from the human IgH locus: (1) The 5' extent of this construct begins at a point ~22 kb upstream of the most proximal $V_h$ segment 6-1; it extends downstream to a point approximately 8.6 kb 3' of the IgHγ1 constant region gene, in a native, germline configuration (the junction between Upstream and Downstream BACs lies in a ~4 kb region beginning approximately ~24-28 kb downstream of the IgHδ constant region, owing to the uncertainty of the recombination crossover junction). This germline-derived segment is followed by the synthetic, human-derived tripartite IgH enhancer. Both zeocin and kanamycin selection markers have been added to the original BAC vector backbone (pBeloBAC11), though they are not critical for transgene function. The entire human-based transgene can be released by digestion with NotI restriction enzyme, releasing a ~231 kb insert.

Example 3: Construction of BAC V12DJCE

This BAC is a derivative of BAC VDJCE, which can be created using standard molecular cloning methods, such as red/ET recombineering (described in Nat. Biotechnol. Vol 21, pp 443-447, (2003), which is hereby incorporated by reference in its entirety). In the instant case, the 12 $V_h$ variable-region gene segments present in pGP69-7 VHC were recombined into the BAC VDJCE, while simultaneously deleting ~25 kb of DNA upstream of the D segment.

The first step in the construction of BAC V12DJCE utilized red/ET recombineering to insert a chloramphenicol resistance cassette downstream of the most proximal $V_h$ element 3-7 in pGP69-7 VHC, in exchange for the VHC homology cassette and the adjacent ampicillin resistance marker present in the vector backbone. In the process, a sequence of 50 bp, homologous to VDJCE sequence was inserted in between $V_h$ 3-7 and the chloramphenicol resistance gene. This resulted in a plasmid which was chloramphenicol resistant and ampicillin sensitive.

The second step in the construction of BAC V12DJCE involved insertion of an ampicillin resistance cassette upstream of the most distal $V_h$ element 1-69. The ampicillin resistance cassette was flanked on either side with flp recombinase-specific FRP recombination signals, and an additional flanking arm of homology added which was also homologous to BAC VDJCE. Plasmid insert was purified from this construct. The insert sequence contained the FRP-flanked ampicillin resistance cassette and all 12 $V_h$ regions, flanked on either end by ~50 bp of sequence homologous to VDJCE BAC, and was isolated by PmeI+ AscI restriction digest for recombination into VDJCE BAC.

The third step in this process involved the recombination of the ~25 kb PmeI+AscI plasmid insert described above into BAC VDJCE. Red/ET mediated recombination resulted in successful incorporation, and the resultant recombination product was selected for growth under ampicillin (from the plasmid insert) and kanamycin (from BAC VDJCE).

The fourth and final step in the construction of V12DJCE involved removal of the ampicillin cassette upstream of the distal $V_h$ element 1-69. Utilizing flp recombinase, the FRP-flanked ampicillin cassette was specifically excised. Selection of proper transformants was ensured by their ability to grow in the presence of kanamycin, but not in the presence of ampicillin. Thus, the final BAC V12DJCE construct differed from BAC VDJCE by the insertion of the 12-$V_h$ elements upstream of the D region, while effecting deletion of a ~25 kb segment of BAC VDJCE. The resultant construct generates a BAC with the 12-$V_h$ elements inserted into VDJCE in their natural germline order; $V_h$ element 1-69 is flanked by ~9 kb of upstream human genomic DNA corresponding to the original 5' end of VDJCE, whereas $V_h$ 3-7 is flanked downstream by ~8 kb of human genomic DNA proximal to the D region.

Example 4: Construction of HCo20 Strain of Transgenic Mice

The HCo20 transgenic mouse strain is the result of a co-injection of minilocus heavy chain transgene pHC2, the germline variable region ($V_h$)-containing YAC yIgH10, and the minilocus construct pVx6.

The pHC2 construct alone is fully capable of being rearranged in vivo to form functional human heavy chain immunoglobulin loci; pVX6 and yIgH10 were added to contribute additional germline $V_H$ diversity. The individual components of the DNA mixture used to produce HCo20 are described below.

The pHC2 insert described above contains four functional human germline $V_H$ gene segments: 1-69 (DP-10), 5-51 (DP-73), 4-34 (DP-63), and 3-30.3 (DP-46). In addition, this construct also contains human genomic sequences comprising 15 functional D segments, all 6 J segments, as well as p4 and y1 constant region segments and a functional p-Y1 switch region.

The pVx6 insert contains 3 human germline $V_H$ segments, $V_H$1-18 (DP-14), $V_H$5-51 (DP-73) and $V_H$3-23 (DP-47). To create the pVx6 construct, an 8.5 kb HindIII/SalI DNA fragment, comprising the germline human $V_H$1-18 (DP-14) gene, together with approximately 2.5 kb of 5'flanking, and 5 kb of 3'flanking genomic sequence, was first subcloned into the plasmid vector pSP72 (Promega) to generate the plasmid p343.7. 16. Next, a 7 kb BamHI/HindIII DNA fragment, comprising the germline human $V_H$5-51 (DP-73) gene, together with approximately 5 kb of 5'flanking and 1 kb of 3'flanking genomic sequence, was cloned into the pBR322 based plasmid cloning vector pGPlf (Taylor et al. (1992) Nucleic Acids Res. 20: 6287-6295), to generate the plasmid p251f. A new cloning vector derived from pGPlf, pGPlk, was then digested with EcoRV/BamHI, and ligated to a 10 kb EcoRV/BamHI DNA fragment, comprising the germline human $V_H$3-23 (DP47) gene, together with approximately 4 kb of 5'flanking and 5 kb of 3'flanking genomic sequence. The resulting plasmid, pl 12. 2RR. 7, was digested with BamHI/SalI and ligated with the 7 kb purified BamHI/SalI insert of p25 If. The resulting plasmid, pVx4, was digested with XhoI and ligated with the 8.5 kb XhoI/SalI insert of p343.7. 16. Afterwards, a clone was obtained with the $V_H$1-18 gene in the same orientation as the other two V genes. This clone, designated pVx6, was then digested with NotI for insert preparation.

YAC yIgH10 was originally identified by PCR screening using $V_h$3 and $V_h$4 family specific primers and is mapped to the human chromosome 14 by $V_h$ content. It was established that yIgH10 contains $V_h$ segments including members of the $V_h$ families $V_h1$, $V_h2$, $V_h3$, and $V_h4$, and in particular at least $V_h1$-18, $V_h1$-24, $V_h2$-26, $V_h3$-15, $V_h3$-20, $V_h3$-21, $V_h3$-23, $V_h3$-30, $V_h3$-30.5, $V_h3$-30.3, $V_h3$-33, $V_h4$-28, $V_h4$-30, $V_h4$-30.4, $V_h4$-30.3, $V_h4$-31, and $V_h4$-34.

Purified inserts from pVx6 (26 kb), pHC2 (80 kb), and yIgH10 (~375 kb) were combined in a 1:1:1 molar ratio, and microinjected into the pronuclei of one-half day (BDF1× KCo5-CMD-JKD) F1 embryos as described by Hogan et al. (B. Hogan et al., Manipulating the Mouse Embryo, A Laboratory Manual, 2nd edition, 1994, Cold Spring Harbor Laboratory Press, Plainview, N.Y.). A founder line of transgenic mice, comprising sequences from pVx6, pHC2 and yIgH10, was established from mice that developed from the injected embryos. This line was designated (HCo20).

The (HCo20) line was then bred with mice comprising the CMD mutation (described in Example 1 of PCT Publication WO 01/09187), the JKD mutation (Chen et al. (1993) EMBO J. 12: 811-820), and the (KCo5) 9272 transgene (Fishwild et al. (1996) Nature Biotechnology 14: 845-851). The resulting mice express human immunoglobulin heavy and kappa light chain transgenes in a background homozygous for disruption of the endogenous mouse heavy and kappa light chain loci.

Example 5: Construction of HCo27 Strain of Transgenic Mice

The HCo27 transgenic mouse strain is the result of a co-injection of minilocus heavy chain transgene pHC2 with the germline variable region ($V_h$)-containing YACs yIgH24a and yIgH10.

As pointed out above, the pHC2 construct alone is fully capable of being rearranged in vivo to form functional human heavy chain immunoglobulin loci; yIgH24 and yIgH10 were added to contribute additional germline $V_H$ diversity. The individual components of the DNA mixture used to produce HCo27 are described below.

The pHC2 and YAC IgH10 constructs are described in detail in Example 4.

The yeast artificial chromosome (YAC) yIgH24a was originally identified by PCR screening using $V_H3$ and $V_H4$ family specific primers and is mapped to the human chromosome, 14 by $V_H$ content. It was established that yIgH24 contains $V_H$ segments including members of the $V_H$ families $V_H1$, $V_H2$, $V_H3$, $V_H4$, and $V_H5$, and in particular at least $V_H1$-24, $V_H1$-45, $V_H1$-46, $V_H2$-26, $V_H3$-30, $V_H3$-30.5, $V_H3$-30.3, $V_H3$-33, $V_H3$-43, $V_H3$-48, $V_H3$-49, $V_H3$-53, $V_H4$-28, $V_H4$-30, $V_H4$-30.4, $V_H4$-30.3, $V_H4$-31, $V_H4$-34, 4-39, and $V_H5$-51.

Purified inserts from pHC2 (80 kb), yIgH10 (~375 kb), and yIgH24a (~460 kb) were combined in a 1:1:1 molar ratio, and microinjected into the pronuclei of one-half day (BDF1×KCo5-CMD-JKD) F1 embryos as described by Hogan et al. (B. Hogan et al., Manipulating the Mouse Embryo, A Laboratory Manual, 2nd edition, 1994, Cold Spring Harbor Laboratory Press, Plainview, N.Y.). A founder line of transgenic mice, comprising sequences from pHC2, yIgH10 and yIgH24a, was established from mice that developed from the injected embryos. This line was designated HCo27.

The HCo27 line was then bred with mice comprising the CMD mutation (described in Example 1 of PCT Publication WO 01/09187), the JKD mutation (Chen et al. (1993) EMBO J. 12: 811-820), and the (KCo5) 9272 transgene (Fishwild et al. (1996) Nature Biotechnology 14: 845-851). The resulting mice express human immunoglobulin heavy and kappa light chain transgenes in a background homozygous for disruption of the endogenous mouse heavy and kappa light chain loci.

Example 6: Construction of HCo28 Strain of Transgenic Mice

The HCo28 transgenic mouse strain is the result of co-injecting three overlapping human Ig heavy chain BAC clone inserts, unmodified from their original germline content: CTD-2304I22, CTD-2572O2, and CTD-2194O15. Together, these span a region of the human IgH locus from $V_h$ segment 3-7 at the 5' end to IgHα1 at the 3' end.

Purified inserts from CTD-2304I22, CTD-2572O2, and CTD-2194O15 were combined in a 1:1:1 molar ratio, and microinjected into the pronuclei of one-half day BDF1× KCo5-CMD-JKD) F1 embryos as described by Hogan et al. (B. Hogan et al., Manipulating the Mouse Embryo, A Laboratory Manual, 2nd edition, 1994, Cold Spring Harbor Laboratory Press, Plainview, N.Y.). A founder line of transgenic mice, comprising sequences from CTD-2304I22, CTD-2572O2, and CTD-2194O15, was established from mice that developed from the injected embryos. This line was designated HCo28.

The HCo28 line was then bred with mice comprising the CMD mutation (described in Example 1 of PCT Publication WO 01/09187), the JKD mutation (Chen et al. (1993) EMBO J. 12: 811-820), and the (KCo5) 9272 transgene (Fishwild et al. (1996) Nature Biotechnology 14: 845-851). The resulting mice express human immunoglobulin heavy and kappa light chain transgenes in a background homozygous for disruption of the endogenous mouse heavy and kappa light chain loci.

Example 7: Construction of HCo30 Strain of Transgenic Mice

The HCo30 transgenic mouse strain is the result of a co-injection of the VDJCE BAC insert and the germline variable region ($V_h$)-containing YAC yIgH24a.

The construction and composition of the VDJCE BAC is described in detail in Example 2, above. The yeast artificial chromosome yIgH24a is described in detail in Example 5, above.

Purified inserts from VDJCE (~231 kb) and yIgH24a (~460 kb) are combined in a 1:1 molar ratio, and microinjected into the pronuclei of one-half day BDF1×KCo5-CMD-JKD) F1 embryos as described by Hogan et al. (B. Hogan et al., Manipulating the Mouse Embryo, A Laboratory Manual, 2nd edition, 1994, Cold Spring Harbor Laboratory Press, Plainview, N.Y.). A founder line of transgenic mice, comprising sequences from VDJCE and yIgH24, is established from mice that develop from the injected embryos. This line is designated HCo30.

The HCo30 line is then bred with mice comprising the CMD mutation (described in Example 1 of PCT Publication WO 01/09187), the JKD mutation (Chen et al. (1993) EMBO J. 12: 811-820), and the (KCo5) 9272 transgene (Fishwild et al. (1996) Nature Biotechnology 14: 845-851). The resulting mice express human immunoglobulin heavy and kappa light chain transgenes in a background homozygous for disruption of the endogenous mouse heavy and kappa light chain loci.

Example 8: Construction of HCo31 Strain of Transgenic Mice

The HCo31 transgenic mouse strain is the result of a co-injection of the VDJCE BAC insert and the CTD-3054M17 BAC insert.

The construction and composition of the VDJCE BAC is described in detail in Example 2, above. BAC CTD-3054M17 is a ~190 kb BAC clone containing human heavy chain Ig $V_h$ segments (from $V_h$4-39 at 5' end to $V_h$3-23 at 3' end), in germline configuration.

Purified inserts from VDJCE (~231 kb) and CTD-3054M17 (~190 kb) are combined in a 1:1 molar ratio, and microinjected into the pronuclei of one-half day BDF1× KCo5-JHD-JKD) F1 embryos as described by Hogan et al. (B. Hogan et al., Manipulating the Mouse Embryo, A Laboratory Manual, 2nd edition, 1994, Cold Spring Harbor Laboratory Press, Plainview, N.Y.). A founder line of transgenic mice, comprising sequences from VDJCE and CTD-3054M17, is established from mice that developed from the injected embryos. This line is designated HCo31.

The HCo31 line is then bred with mice comprising the CMD mutation (described in Example 1 of PCT Publication WO 01/09187), the JKD mutation (Chen et al. (1993) EMBO J. 12: 811-820), and the (KCo5) 9272 transgene (Fishwild et al. (1996) Nature Biotechnology 14: 845-851). The resulting mice express human immunoglobulin heavy and kappa light chain transgenes in a background homozygous for disruption of the endogenous mouse heavy and kappa light chain loci.

Example 9: Construction of HCo32 Strain of Transgenic Mice

The HCo32 transgenic mouse strain is the result of a co-injection of the VDJCE BAC insert and the pGP69-7 VHC insert.

The construction and composition of the VDJCE BAC is described in detail in Example 2, above. The construction and composition of pGP69-7 VHC is described in detail in Example 1, above.

Purified inserts from VDJCE BAC (~231 kb) and the pGP69-7 VHC (~28 kb) are combined in a 1:1 molar ratio, and microinjected into the pronuclei of one-half day BDF1× KCo5-CMD-JKD) F1 embryos as described by Hogan et al. (B. Hogan et al., Manipulating the Mouse Embryo, A Laboratory Manual, 2nd edition, 1994, Cold Spring Harbor Laboratory Press, Plainview, N.Y. (which is hereby incorporated by reference in its entirety). A founder line of transgenic mice, comprising sequences from VDJCE and pGP69-7 VHC, is established from mice that developed from the injected embryos. This line is designated HCo32.

The HCo32 line is then bred with mice comprising the CMD mutation (described in Example 1 of PCT Publication WO 01/09187), the JKD mutation (Chen et al. (1993) EMBO J. 12: 811-820), and the (KCo5) 9272 transgene (Fishwild et al. (1996) Nature Biotechnology 14: 845-851). The resulting mice express human immunoglobulin heavy and kappa light chain transgenes in a background homozygous for disruption of the endogenous mouse heavy and kappa light chain loci.

Example 10: Construction of HCo33 Strain of Transgenic Mice

The HCo33 transgenic mouse strain is the result of injecting the V12DJCE BAC insert.

The construction of the V12DJCE BAC which contains the 12 $V_h$ segments derived from pGP69-7 VHC integrated into the VDJCE BAC approx ~8 kb upstream of the D region, is described in detail in Example 3, above.

Purified insert from V12DJCE is microinjected into the pronuclei of one-half day BDF1×KCo5-CMD-JKD) F1 embryos as described by Hogan et al. (B. Hogan et al., Manipulating the Mouse Embryo, A Laboratory Manual, 2nd edition, 1994, Cold Spring Harbor Laboratory Press, Plainview, N.Y.). A founder line of transgenic mice, comprising sequences from V12DJCE, is established from mice that developed from the injected embryos. This line is designated HCo33.

The HCo33 line is then bred with mice comprising the CMD mutation (described in Example 1 of PCT Publication WO 01/09187), the JKD mutation (Chen et al. (1993) EMBO J. 12: 811-820), and the (KCo5) 9272 transgene (Fishwild et al. (1996) Nature Biotechnology 14: 845-851). The resulting mice express human immunoglobulin heavy and kappa light chain transgenes in a background homozygous for disruption of the endogenous mouse heavy and kappa light chain loci.

Example 11: Construction of HCo34 Strain of Transgenic Mice

The HCo34 transgenic mouse strain is the result of injecting pIgYBAC insert.

The pIgYBAC construct is a ~500 kb bacterial-yeast shuttle vector containing all relevant $V_h$ segments from yIgH10 plus the entire VDJCE BAC. The YAC yIgH10 is described in detail in Example 5, above. The VDJCE BAC is described in detail in Example 2, above.

Purified insert from pIgYBAC (~500 kb) is microinjected into the pronuclei of one-half day BDF1×KCo5-CMD-JKD) F1 embryos as described by Hogan et al. (B. Hogan et al., Manipulating the Mouse Embryo, A Laboratory Manual, 2nd edition, 1994, Cold Spring Harbor Laboratory Press, Plainview, N.Y.). A founder line of transgenic mice, comprising sequences from pIgYBAC, is established from mice that developed from the injected embryos. This line is designated HCo34.

The HCo34 line is then bred with mice comprising the CMD mutation (described in Example 1 of PCT Publication WO 01/09187), the JKD mutation (Chen et al. (1993) EMBO J. 12: 811-820), and the (KCo5) 9272 transgene (Fishwild et al. (1996) Nature Biotechnology 14: 845-851). The resulting mice express human immunoglobulin heavy and kappa light chain transgenes in a background homozygous for disruption of the endogenous mouse heavy and kappa light chain loci.

Example 12: Balb/c Strain Introduction

The original HuMab mice were comprised of a mixed strain background; genetic contributions from C57Bl/6J, CBA/J, DBA/2J, and 129/Sv strains are all known to have occurred during the generation of fully functional HuMab mice. The major histocompatibility complex (MHC) haplotypes for these parental strains are b, k, d and b, respectively. However, routine surveys of the HuMab population revealed a preponderance of the b and k haplotypes following multiple generations of non-selective breeding. The Balb/c strain (MHC haplotype d) is known to be a 'high responder' in terms of antibody responsiveness, compared to the aforementioned strains (see for example Agents and Actions, v. 4 no. 4, pp 277-285 (1974)). In addition to the superior antibody responsiveness, presence of the Balb/c strain also ensures that the d MHC haplotype is present. It is known that antigen presentation by MHC is sometimes dependent on MHC haplotype, and therefore strains with a higher MHC diversity may be better equipped to present diverse antigens and to generate antigen-specific antibody responses. In an effort to impart the beneficial aspects of the Balb/c background onto existing HuMab strains, a genetic cross strategy was carried out. The KCo5 strain (as described in Fishwild et al. (1996) Nature Biotechnology 14:845-851) was repeatedly backcrossed to wild-type Balb/c mice; after 5 generations of backcrossing, mice selected for the presence of the KCo5 light chain transgene, heavy chain gene disruption (as described in Example 1 of PCT Publication WO 01/09187, which is hereby incorporated by reference in its entirety), and κ light chain gene disruption (as described in Chen et al. (1993) EMBO J. 12:811-820) were intercrossed. Offspring of this intercross were then crossed to each other to generate mice which were homozygous for the heavy chain and κ light chain gene disruptions. Some of the resultant mice carried the KCo5 transgene, others did not; two separate lines (one containing KCo5, the other not) were then created and expanded, collectively referred to as KCo5 [M/K] (Balb). In order to generate HuMab mice with the salutary effects of the Balb/c strain, the KCo5 [M/K] (Balb) mice were crossed to HuMab mice of the mixed strain background. The resulting mice are homozygous for both heavy and κ light chain gene disruptions, contain at least one chromosomal copy of the human heavy and light chain transgenes, and are approximately ~50% Balb/c genetically. This hybrid breeding scheme allows for the following: 1) multiple different HuMab strains (HCo7, HCo12, HCo17, etc) of mixed strain background can be crossed to the same KCo5 [M/K] (Balb) strain; 2) the d MHC haplotype from Balb/c is present in all hybrid offspring, in addition to either b or k haplotypes contributed from the HuMab mixed strain, for maximum haplotype diversity; 3) separation of the mixed strain HuMab population from the KCo5 [M/K] (Balb) population until the final genetic cross ensures that the hybrid offspring are more consistent generation-to-generation than non-directed, successive intercrosses which can be subject to genetic drift.

In an approach which is directly analogous to the one described above, the Balb/c genetic background was also bred into KCo5 mice harboring the same κ light gene disruption, but with a different heavy chain gene disruption (so called J or JHD disruption; see U.S. Pat. No. 5,545,806 for description, which is hereby incorporated by reference in its entirety). Again, Balb/c mice homozygous for both heavy and light chain gene disruptions were created, some containing the KCo5 transgene, others not, and were collectively referred to as KCo5 [J/K] (Balb). This strain can also be crossed to all types of HuMab mice of mixed strain background to create hybrids as described above.

As shown in FIG. 4, the hybrid mice resulting from HCo12 crosses to KCo5[J/K](Balb) have substantially higher total immunoglobulin in the naïve or pre-immune state, and also show an elevated antigen-specific immunoglobulin titer against the tetanus toxoid (TT) antigen relative to the parental HCo12 strain. Use of this strategy has resulted in Balb/c hybrids being created for HCo7, HCo12, HCo17, and HCo20 strains; the strategy is further amenable to hybrid crosses onto all current and future HuMab mouse lines, such as HCo27, HCo28, HCo30, HCo31, HCo32, and HCo33 described herein.

Example 13: HCo7/Lambda Strain Introduction

The creation of the HCo7/lambda transgenic mouse strain involved the homozygous disruption of the endogenous mouse kappa light chain gene as described in Chen et al. (1993) EMBO J. 12:811-820 (which is hereby incorporated by reference in its entirety), as the homozygous disruption of the endogenous mouse heavy chain gene as described in Example 1 of PCT Publication WO 01/09187 (which is hereby incorporated by reference in its entirety). The HC07/lambda transgenic mouse strain also carries a human kappa light chain transgene, KCo5, as described in Fishwild et al. (1996) Nature Biotechnology 14:845-851 (which is hereby incorporated by reference in its entirety), and a human heavy chain transgene, HCo7, as described in U.S. Pat. Nos. 5,545,806; 5,625,825; and 5,545,807 (which are hereby incorporated by reference in their entirety). This transgenic mouse strain also carries a human lambda light chain transgene composed of a yeast artificial chromosome containing most of the human Ig lambda locus, as described in PCT Publication WO 2000/26373 (which is hereby incorporated by reference in its entirety). However, this transgenic mouse strain does not carry a disrupted endogenous λ light chain locus. Through selective breeding, progeny have been recovered which harbor homozygous gene disruptions of both heavy and light chains, contain the human heavy chain transgene, and in terms of light chain transgenes, contain either both κ and λ light chain transgenes, only the κ light chain transgene, or only the λ light chain transgene. All three genotypes can be used for immunizations and recovery of human antibodies as described in detail above.

Example 14: Construction of BAC V12DJCE-neo

This BAC is a derivative of BAC V12DJCE, which can be created using standard molecular cloning methods, such as red/ET recombineering (described in Nat. Biotechnol. Vol 21, pp 443-447, (2003), which is hereby incorporated by reference in its entirety). In the instant case, a selectable resistance marker from the neomycin resistance gene cassette (hereafter referred to as neo), operably linked to a dual prokaryotic and eukaryotic promoter/enhancer element, was inserted ~10 kb upstream of the 12 $V_h$ variable-region gene segments present in BAC V12DJCE.

The first step in the construction of BAC V12DJCE-neo utilized red/ET recombineering to insert an ampicillin resistance cassette in exchange for the existing kanamycin resistance gene in V12DJCE.

The second step in the construction of BAC V12DJCE-neo involved exchange of the ampicillin resistance cassette from the first step for a hybrid cassette referred to as PGK-gb2-neo. This resistance cassette utilizes a hybrid prokaryotic/eukaryotic promoter that will allow for expression of the neo cassette in both prokaryotic (i.e. bacterial) and eukaryotic cells. The neo cassette confers resistance to both kanamycin (for prokaryotic selection) and neomycin (commonly interchangeable with G418, for eukaryotic selection).

In all other aspects, the V12DJCE-neo construct is identical to the parent molecule V12DJCE; specifically, immunoglobulin gene content is entirely preserved between the two constructs.

Example 15: Construction of HCo37 Strain of Transgenic Mice

The HCo37 transgenic mouse strain is the result of injecting or transfecting the V12DJCE-neo BAC insert.

The construction of the V12DJCE-neo BAC which contains the PGK-gb2-neo resistance cassette integrated into the V 12DJCE BAC approx ~10 kb upstream of the proximal Vh segment 1-69, is described in detail in Example 14, above.

Purified insert from V12DJCE is microinjected into the pronuclei of one-half day BDF1×KCo5-CMD-JKD) F1 embryos as described by Hogan et al. (B. Hogan et al., Manipulating the Mouse Embryo, A Laboratory Manual, 2nd edition, 1994, Cold Spring Harbor Laboratory Press, Plainview, N.Y.). A founder line of transgenic mice, comprising sequences from V12DJCE-neo, is established from mice that developed from the injected embryos. This line is designated HCo37.

In an alternative application, the V12DJCE-neo construct is used to transfect mouse embryonic stem (ES) cells as described by Hogan et al. (B. Hogan et al., Manipulating the Mouse Embryo, A Laboratory Manual, 2nd edition, 1994, Cold Spring Harbor Laboratory Press, Plainview, N.Y.). ES cells undergoing stable and permanent integration of this DNA construct can be identified and clonally propagated using the selection agent G418. Individual ES cell clones harboring the V12DJCE-neo construct can then be used to create chimeric mice by injection of the modified ES cells into morula- or blastocyst-stage mouse embryos, and developing them to term. Such chimeric mice can then be bred to other mice to confirm transmission of the transfected V12DJCE-neo construct to offspring. This line is designated HCo37.

The HCo37 line is then bred with mice comprising the CMD mutation (described in Example 1 of PCT Publication WO 01/09187), the JKD mutation (Chen et al. (1993) EMBO J. 12: 811-820), and the (KCo5) 9272 transgene (Fishwild et al. (1996) Nature Biotechnology 14: 845-851). The resulting mice express human immunoglobulin heavy and kappa light chain transgenes in a background homozygous for disruption of the endogenous mouse heavy and kappa light chain loci.

What is claimed is:

1. A bacterial artificial chromosome for use in the preparation of transgenic non-human mammals capable of producing human immunoglobulin, the bacterial artificial chromosome comprising, in operable linkage, an unrearranged human IgM locus sequence in germline configuration that begins about 22 kilobases upstream of variable heavy chain region gene $V_H6$-1 and extends about 8.6 kilobases downstream of an IgHγ1 constant region gene, operably linked to a synthetic tripartite IgH enhancer comprising human enhancer elements Hs3, Hs1,2 and Hs4.

2. A non-human animal that carries the bacterial artificial chromosome according to claim 1.

3. The non-human animal according to claim 2, which is a rodent.

4. The non-human animal according to claim 3, wherein the rodent is a mouse.

5. A transgenic mouse containing, integrated into its genome, the bacterial artificial chromosome according to claim 1.

6. A transgenic mouse according to claim 5, wherein the mouse is cross-bred to the Balb/c strain.

7. A method of producing human antibodies having desired properties from a transgenic mouse, the method comprising:
   contacting the transgenic mouse with a pre-selected antigen; and
   collecting human antibodies that bind to the pre-selected antigen, wherein the transgenic mouse carries in its genome:
   (i) a bacterial artificial chromosome comprising, in operable linkage, an unrearranged human IgM locus sequence in germline configuration that begins about 22 kilobases upstream of variable heavy chain region gene $V_H6$-1 and extends about 8.6 kilobases downstream of an IgHγ1 constant region gene, operably linked to a synthetic tripartite IgH enhancer comprising human enhancer elements Hs3, Hs1,2 and Hs4; and
   (ii) a human immunoglobulin light chain transgene,
   such that the transgenic mouse makes human antibodies.

* * * * *

UNITED STATES PATENT AND TRADEMARK OFFICE
CERTIFICATE OF CORRECTION

PATENT NO. : 9,693,539 B2  
APPLICATION NO. : 12/672883  
DATED : July 4, 2017  
INVENTOR(S) : Daniel K. Rohrer, Amelia N. Black and Nils Lonberg Page 1 of 1

It is certified that error appears in the above-identified patent and that said Letters Patent is hereby corrected as shown below:

On the Title Page

(75) Inventors:
"(US); Nancy Amelia Black, Los Gatos, CA" should read -- (US); Amelia N. Black, Los Gatos, CA --

Signed and Sealed this  
Fourteenth Day of November, 2017

Joseph Matal  
*Performing the Functions and Duties of the*  
*Under Secretary of Commerce for Intellectual Property and*  
*Director of the United States Patent and Trademark Office*

```
                            SEQUENCE LISTING

<160> NUMBER OF SEQ ID NOS: 39

<210> SEQ ID NO 1
    <211> LENGTH: 11
    <212> TYPE: DNA
    <213> ORGANISM: Artificial sequence
    <220> FEATURE:
    <223> OTHER INFORMATION: Synthetic oligonucleotide

<400> SEQUENCE: 1
ctaactgggg a                                                           11

<210> SEQ ID NO 2
    <211> LENGTH: 11
    <212> TYPE: DNA
    <213> ORGANISM: Artificial sequence
    <220> FEATURE:
    <223> OTHER INFORMATION: Synthetic oligonucleotide
    <220> FEATURE:
    <221> NAME/KEY: misc_feature
    <222> LOCATION: (5)..(5)
    <223> OTHER INFORMATION: n is a, t or g

<400> SEQUENCE: 2
ctaantgggg a                                                           11

<210> SEQ ID NO 3
    <211> LENGTH: 10
    <212> TYPE: DNA
    <213> ORGANISM: Artificial sequence
    <220> FEATURE:
    <223> OTHER INFORMATION: Synthetic oligonucleotide

<400> SEQUENCE: 3
ctaactggga                                                             10

<210> SEQ ID NO 4
    <211> LENGTH: 4
    <212> TYPE: PRT
    <213> ORGANISM: Artificial sequence
    <220> FEATURE:
    <223> OTHER INFORMATION: Synthetic polypeptide

<400> SEQUENCE: 4

Lys Glu Arg Val
    1

<210> SEQ ID NO 5
```

```
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 5

Asn Asp Ser Val
1

<210> SEQ ID NO 6
<211> LENGTH: 12
<212> TYPE: RNA
<213> ORGANISM: Artificial sequence
<220> FEATURE:
<223> OTHER INFORMATION: Synthetic oligonucleotide

<400> SEQUENCE: 6
aaagaaagag uu                                                           12

<210> SEQ ID NO 7
<211> LENGTH: 12
<212> TYPE: RNA
<213> ORGANISM: Artificial sequence
<220> FEATURE:
<223> OTHER INFORMATION: Synthetic oligonucleotide

<400> SEQUENCE: 7
aacgacagcg uu                                                           12

<210> SEQ ID NO 8
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 8
gtcgacttgg taattatttt gggagc                                            26

<210> SEQ ID NO 9
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 9
aacaggtcag gtaaaccaga agtaagataa gc                                     32

<210> SEQ ID NO 10
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 10
tctggtttac ctgacctgtt atagagtttt tg                                     32

<210> SEQ ID NO 11
<211> LENGTH: 31
<212> TYPE: DNA
<213> ORGANISM: Artificial sequence
<220> FEATURE:
<223> OTHER INFORMATION: Synthetic oligonucleotide
```

<400> SEQUENCE: 11
agcaccttct acaggagtgg gtggcttaaa c                                    31

<210> SEQ ID NO 12
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 12
ccactcctgt agaaggtgct ggggttgaca c                                    31

<210> SEQ ID NO 13
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 13
gatgataaac tttctccacg tttgccagac c                                    31

<210> SEQ ID NO 14
<211> LENGTH: 35
<212> TYPE: DNA
<213> ORGANISM: Artificial sequence
<220> FEATURE:
<223> OTHER INFORMATION: Synthetic oligonucleotide

<400> SEQUENCE: 14
cgtggagaaa gtttatcatc tttcaattaa gcctc                                35

<210> SEQ ID NO 15
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 15
ctcgagattt tccaggcaat agtgagtg                                        28

<210> SEQ ID NO 16
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 16
gtcgacgagt ttttgtctga agttctcac                                       29

<210> SEQ ID NO 17
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 17
aatgtagacc gtctgaatgt agaagatcaa gg                                   32

<210> SEQ ID NO 18
<211> LENGTH: 36

```
<212> TYPE: DNA
<213> ORGANISM: Artificial sequence
<220> FEATURE:
<223> OTHER INFORMATION: Synthetic oligonucleotide

<400> SEQUENCE: 18
acattcagac ggtctacatt tttcaaatca ttcacc                                36

<210> SEQ ID NO 19
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 19
tcatgttggt ggtgattaag cagcttcagc                                       30

<210> SEQ ID NO 20
<211> LENGTH: 34
<212> TYPE: DNA
<213> ORGANISM: Artificial sequence
<220> FEATURE:
<223> OTHER INFORMATION: Synthetic oligonucleotide

<400> SEQUENCE: 20
cttaatcacc accaacatga gaaatgtatg acac                                  34

<210> SEQ ID NO 21
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 21
tttccatttg gaaaatgggg agagaagg                                         28

<210> SEQ ID NO 22
<211> LENGTH: 35
<212> TYPE: DNA
<213> ORGANISM: Artificial sequence
<220> FEATURE:
<223> OTHER INFORMATION: Synthetic oligonucleotide

<400> SEQUENCE: 22
ccccattttc caaatggaaa tttagacaag cacgg                                 35

<210> SEQ ID NO 23
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 23
ctcgagacga caacaggaga gtcc                                             24

<210> SEQ ID NO 24
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 24
```
gtcgactctg tgagatcaga caggaacc                                              28

<210> SEQ ID NO 25
<211> LENGTH: 30
<212> TYPE: DNA
<213> ORGANISM: Artificial sequence
<220> FEATURE:
<223> OTHER INFORMATION: Synthetic oligonucleotide

<400> SEQUENCE: 25
ggttcacgag ggagagtcta ttcatatggg                                            30

<210> SEQ ID NO 26
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 26
agactctccc tcgtgaaccc tagttctcac c                                          31

<210> SEQ ID NO 27
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 27
ttcctcagcc tccaaacctc agcatcactc ag                                         32

<210> SEQ ID NO 28
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 28
gaggtttgga ggctgaggaa gagcaagaaa gag                                        33

<210> SEQ ID NO 29
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 29
cttcaaaatg tgcacagaag acaagagtgt cc                                         32

<210> SEQ ID NO 30
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 30
cttctgtgca cattttgaag ctgagttgca gg                                         32

<210> SEQ ID NO 31
<211> LENGTH: 26
<212> TYPE: DNA
<213> ORGANISM: Artificial sequence

```
<220> FEATURE:
<223> OTHER INFORMATION: Synthetic oligonucleotide

<400> SEQUENCE: 31
ctcgagaaga caacaggagt gtccag                                          26

<210> SEQ ID NO 32
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 32
gcggccgcct gtttactctg atggtagtt                                       29

<210> SEQ ID NO 33
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 33
ggcgcgccgt tcctagccaa gggaagcgg                                       29

<210> SEQ ID NO 34
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 34
acgcgttcct gaccgctgag ccct                                            24

<210> SEQ ID NO 35
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 35
gtcgacctgg aaagccctag ctga                                            24

<210> SEQ ID NO 36
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 36
ctcgagcgtt ggctcccctg ccct                                            24

<210> SEQ ID NO 37
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 37
gatatcctgg cctttttgcca gtcctc                                         26
```

```
<210> SEQ ID NO 38
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 38
cccgggacgc tcgctgcccc actc                                              24

<210> SEQ ID NO 39
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 39
ggcgcgcctg ggacctccat gcagg                                             25
```